(12) United States Patent
Bunnage et al.

(10) Patent No.: US 6,407,114 B1
(45) Date of Patent: Jun. 18, 2002

(54) PYRAZOLOPYRIMIDINONE CGMP PDE5 INHIBITORS FOR THE TREATMENT OF SEXUAL DYSFUNCTION

(75) Inventors: Mark Edward Bunnage; John Paul Mathias; Stephen Derek Albert Street; Anthony Wood, all of Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/425,095

(22) Filed: Oct. 22, 1999

(30) Foreign Application Priority Data

Oct. 23, 1998 (GB) ............................. 9823103

(51) Int. Cl.$^7$ ....................... A61K 31/517; A61P 15/10; A61P 13/08; C07D 487/04
(52) U.S. Cl. ..................... 514/258; 544/262; 544/118; 544/61; 514/234.5; 514/228.5
(58) Field of Search .................. 514/258; 544/262; 546/119, 120

(56) References Cited

U.S. PATENT DOCUMENTS

| | | | |
|---|---|---|---|
| 4,663,326 A | 5/1987 | Hamilton | 514/258 |
| 4,666,908 A | 5/1987 | Hamilton | 514/229 |
| 4,871,843 A | 10/1989 | Rgoer et al. | 540/575 |
| 5,250,534 A | 10/1993 | Bell et al. | 514/258 |
| 5,272,147 A | 12/1993 | Bell et al. | 514/234.2 |
| 5,294,612 A | 3/1994 | Bacon et al. | 514/234.2 |
| 5,346,901 A | 9/1994 | Bell et al. | 514/258 |
| 5,426,107 A | 6/1995 | Bell et al. | 514/234.2 |
| 5,719,283 A | 2/1998 | Bell et al. | 544/262 |
| 5,734,053 A | 3/1998 | Terrett | 544/277 |
| 5,736,548 A | 4/1998 | Bacon et al. | 514/258 |
| 5,955,611 A | 9/1999 | Dunn et al. | 544/262 |

FOREIGN PATENT DOCUMENTS

| | | |
|---|---|---|
| EP | 0463756 | 1/1992 |
| EP | 0349239 | 3/1994 |
| EP | 0636626 | 2/1995 |
| EP | 0526004 | 8/1997 |
| WO | WO9306104 | 4/1993 |
| WO | 9307144 | * 4/1993 |
| WO | WO9307149 | 4/1993 |
| WO | WO9312095 | 6/1993 |
| WO | WO9400453 | 1/1994 |
| WO | WO9405661 | 3/1994 |
| WO | WO9428902 | 12/1994 |
| WO | WO9616644 | 6/1996 |
| WO | 9616657 | * 6/1996 |
| WO | WO9628429 | 9/1996 |
| WO | WO9628448 | 9/1996 |
| WO | WO9849166 | 11/1998 |
| WO | WO9954333 | 10/1999 |

OTHER PUBLICATIONS

Czamiecki et al. in Annual Reports in Medicinal Chemistry, 31, 61–70, 1996.*
DuMaitre et al., J. Med. Chem., 39(8), 1996, 1635–1644.
Dumaitre et al. J. Med. Chem., 1996, 39, 1635–1644.
JP 8 253484 Abstract 08253484, Oct. 1996.
Harriet W. Hamilton, et al., J. Med. Chem, 1987, 30, pp. 96–96.

* cited by examiner

*Primary Examiner*—Mukund J. Shah
*Assistant Examiner*—Venkataraman Balasubramanian
(74) *Attorney, Agent, or Firm*—Peter C. Richardson; Gregg C. Benson; James T. Jones

(57) ABSTRACT

There is provided compounds of formula IA and of formula IB,

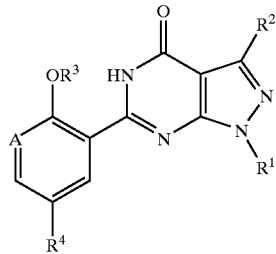

IA

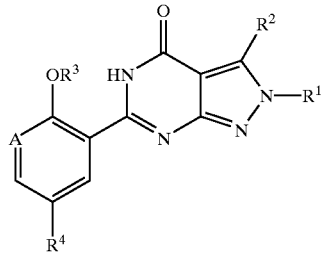

IB wherein $R^1$, $R^2$, $R^3$, $R^4$ and A have meanings given in the description, which are useful in the curative and prophylactic treatment of a medical condition for which inhibition of a cyclic guanosine 3',5'-monophosphate phosphodiesterase (e.g. cGMP PDE5) is desired.

17 Claims, No Drawings

PYRAZOLOPYRIMIDINONE CGMP PDE5 INHIBITORS FOR THE TREATMENT OF SEXUAL DYSFUNCTION

FIELD OF THE INVENTION

This invention relates to pharmaceutically useful compounds, in particular compounds which are useful in the inhibition of cyclic guanosine 3',5'-monophosphate phosphodiesterases (cGMP PDEs), such as type 5 cyclic guanosine 3',5'-monophosphate phosphodiesterase (cGMP PDEs). The compounds therefore have utility in a variety of therapeutic areas, including male erectile dysfunction (MED).

PRIOR ART

International patent application WO 93/07149 discloses certain pyrazolo[3,4-d]pyrimidinone compounds as anti-anginal agents. International patent application WO 96/16657 discloses the use of these compounds (amongst others) in the treatment of MED.

DISCLOSURE OF THE INVENTION

According to the invention there is provided compounds of formulae IA and IB:

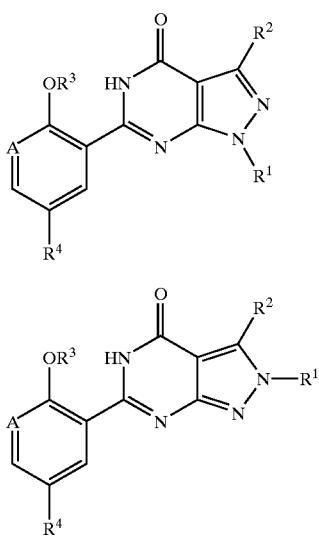

wherein

A represents CH or N;

$R^1$ and $R^2$ independently represent H, lower alkyl, Het, alkylHet, aryl or alkylaryl, which latter five groups are all optionally substituted (and/or, in the case of lower alkyl, optionally terminated) by one or more substituents selected from halo, cyano, nitro, lower alkyl, $OR^5$, $C(O)R^6$, $C(O)OR^7$, $C(O)NR^8R^9$, $NR^{10a}R^{10b}$ and $SO_2NR^{11a}R^{11b}$;

$R^3$ represents H or lower alkyl, which latter group is optionally substituted and/or optionally terminated by one or more substituents selected from aryl, Het, halo, cyano, nitro, $OR^5$, $C(O)R^6$, $C(O)OR^7$, $C(O)NR^8R^9$ and $NR^{10a}R^{10b}$ and $SO_2NR^{11a}R^{11b}$;

$R^4$ represents $SO_2NR^{12}R^{13}$;

$R^{12}$ and $R^{13}$, together with the nitrogen to which they are attached, form Het;

Het represents an optionally-substituted four- to twelve-membered heterocyclic group, which group contains at least one nitrogen atom and, optionally, one or more further heteroatoms selected from nitrogen, sulphur and oxygen; and $R^5$, $R^6$, $R^7$, $R^8$, $R^9$, $R^{10a}$, $R^{10b}$, $R^{11a}$ and $R^{11b}$ independently represent, at each occurrence when used herein, H or lower alkyl; or a pharmaceutically, or a veterinarily, acceptable derivative thereof; provided that the compound is not:

6-[2-ethoxy-5-(4-methyl-1-piperazinylsulphonyl) phenyl]-1-n-propyl-1,5-dihydro-4H-pyrazolo[3,4-d] pyrimidin-4-one; or 3-methyl-6-[5-(morpholinosulphonyl)-2-n-propoxyphenyl]-1-n-propyl-1,5-dihydro-4H-pyrazolo[3,4-d]pyrimidin-4-one;

which compounds are referred to together hereinafter as "the compounds of the invention".

The term "aryl", when used herein, includes six- to ten-membered carbocyclic aromatic groups, such as phenyl and naphthyl, which groups are optionally substituted with one or more substituents selected from aryl, lower alkyl, Het, halo, cyano, nitro, $OR^5$, $C(O)R^6$, $C(O)OR^7$, $C(O)NR^8R^9$, $NR^{10a}R^{10b}$, $SO_2NR^{11a}R^{11b}$ and $N(H)SO_2R^{11a}$.

The term "Het", when used herein, includes four- to twelve-membered, preferably four- to ten-membered, ring systems, which may be wholly or partly aromatic in character. Each "Het" group identified herein is optionally substituted by one or more substituents selected from halo, cyano, nitro, lower alkyl (which alkyl group may itself be optionally substituted or terminated a defined below for $R^{14}$), $OR^5$, $C(O)R^6$, $C(O)OR^7$, $C(O)NR^8R^9$ and $NR^{10a}R^{10b}$, $SO_2NR^{11a}R^{11b}$ and $N(H)SO_2R^{11a}$. The term thus includes groups such as optionally substituted azetidinyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, pyridinyl, quinolinyl, isoquinolinyl, piperidinyl, pyrazolyl imidazopyridinyl and piperazinyl, e.g. 4-$R^{14}$-piperazinyl, wherein $R^{14}$ represents H or lower alkyl, which alkyl group is optionally substituted or terminated by one or more substituents selected from aryl, Het, halo, cyano, nitro, $OR^5$, $C(O)R^6$, $C(O)OR^7$, $C(O)NR^8R^9$, $NR^{10a}R^{10b}$, $SO_2NR^{11a}R^{11b}$ and $N(H)SO_2R^{11a}$.

"Het" groups may also be in the form of an N-oxide.

For the avoidance of doubt, the nitrogen atom to which $R^{12}$ and $R^{13}$ are attached is the nitrogen atom that must be present in the relevant Het group.

The term "lower alkyl", when used herein, includes $C_{1-6}$ alkyl. Alkyl groups which $R^1$, $R^2$, $R^3$, $R^5$, $R^6$, $R^7$, $R^8$, $R^9$, $R^{10a}$, $R^{10b}$, $R^{11a}$, $R^{11b}$ and $R^{14}$ may represent, and with which $R^1$, $R^2$ and Het may be substituted, may, when there is a sufficient number of carbon atoms, be linear or branched, be saturated or unsaturated, be cyclic, acyclic or part cyclic/acyclic, be interrupted by oxygen and/or be substituted by one or more halo atom.

The terms "alkylHet" and "alkylaryl" include $C_{1-6}$ alkylHet and $C_{1-6}$ alkylaryl. The alkyl groups (e.g. the $C_{1-6}$ alkyl groups) of alkylHet and alkylaryl may, when there is a sufficient number of carbon atoms, be linear or branched, be saturated or unsaturated, and/or be interrupted by oxygen. When used in this context, the terms "Het" and "aryl" are as defined hereinbefore.

Halo groups with which $R^1$, $R^2$, $R^3$, $R^{14}$, aryl, Het and above-mentioned alkyl groups may be substituted or terminated include fluoro, chloro, bromo and iodo.

Pharmaceutically, and veterinarily, acceptable derivatives includes salts and solvates. Salts which may be mentioned include: acid addition salts, for example, salts formed with inorganic acids such as hydrochloric, hydrobromic, sulphuric and phosphoric acid, with carboxylic acids or with organo-sulphonic acids; base addition salts; metal salts formed with bases, for example, the sodium and potassium salts. Pharmaceutically acceptable derivatives also include $C_1$ to $C_4$ alkyl ammonium salts.

Preferred compounds of the invention include those wherein, when the compound is a compound of formula IA, in which $R^1$ represents $C_{1-6}$ alkyl, $R^2$ represents H, methyl or ethyl, $R^3$ represents $C_{2-4}$ alkyl and A represents CH, then $R^{12}$ and $R^{13}$, together with the nitrogen to which they are attached, do not form a pyrrolidinyl, piperidinyl, morpholinyl, 1-imidazoyl or a 4-$R^{14}$-piperazinyl (in which $R^{14}$ represents H, $C_{1-3}$ alkyl or hydroxy$C_{2-3}$alkyl) group, which heterocyclic groups are optionally substituted by one or two $C_{1-4}$ alkyl groups.

Further preferred compounds of the invention include those wherein, when A represents CH, $R^2$ does not represent lower alkyl or H.

Further preferred compounds of the invention include those wherein, when A represents N, $R^1$ represents lower alkyl and $R^2$ represents lower alkyl, Het, alkylHet, aryl or alkylaryl.

Preferred compounds of the invention include those wherein:

$R^1$ represents linear, branched, cyclic, or acyclic, lower alkyl, Het or alkylHet;

$R^2$ represents linear or branched, cyclic, acyclic, or part-cyclic, lower alkyl (which alkyl group is optionally terminated by OH), alkylHet or alkylaryl (the alkyl group of both of which is optionally interrupted by an O atom), aryl or Het;

$R^3$ represents linear or branched lower alkyl, optionally terminated by $OR^5$, where $R^5$ represents H or methyl;

$R^{12}$ and $R^{13}$ together with the nitrogen atom to which they are attached, represent 4-$R^{14}$-piperazinyl, in which $R^{14}$ is as hereinbefore defined.

More preferred compounds of the invention include those wherein:

$R^1$ represents linear or cyclic $C_{2-5}$ alkyl, Het or $C_{1-3}$ alkylHet, in which both latter cases, Het represents a six-membered aromatic ring containing one or two nitrogen atoms;

$R^2$ represents linear or branched, cyclic, acyclic or part-cyclic $C_{1-4}$ alkyl (which alkyl group is optionally terminated by OH), $C_{1-3}$ alkylHet (in which Het represents a six-membered heterocyclic group containing one or two nitrogen atoms), $C_{1-3}$ alkylaryl (the alkyl group of which is optionally interrupted by an O atom), aryl or Het (in which Het represents a six-membered heterocyclic group containing one or two nitrogen atoms);

$R^3$ represents linear or branched $C_{1-4}$ alkyl, optionally terminated by $OR^5$, where $R^5$ represents H or methyl;

$R^{12}$ and $R^{13}$, together with the nitrogen atom to which they are attached, represent 4-$R^{14}$-piperazinyl, in which $R^{14}$ represents lower alkyl, optionally terminated by OH.

Particularly preferred compounds of the invention include those wherein:

$R^1$ represents ethyl, n-propyl or cyclopentyl, —$CH_2$-Het (in which Het represents pyridin-2-yl) or pyrimidin-2-yl;

$R^2$ represents methyl, hydroxymethyl, ethyl, propyl or cyclopropylmethyl, —$CH_2$Het (where Het is pyridin-2-yl, pyrimidin-2-yl, morpholinyl or pyrazin-2-yl), benzyl, —$CH_2OCH_2$-phenyl, phenyl or pyrazin-2-yl;

$R^3$ represents linear or branched $C_{2-3}$ alkyl, optionally terminated by $OCH_3$;

$R^{12}$ and $R^{13}$, together with the nitrogen atom to which they are attached, represent 4-$R^{14}$-piperazinyl, in which $R^{14}$ represents $C_{1-3}$ alkyl optionally terminated by OH.

Most preferred compounds of the invention include the compounds of Examples 1 to 25 described hereinafter.

The compounds of the invention may exhibit tautomerism. All tautomeric forms of the compounds of formulae IA and IB, and mixtures thereof, are included within the scope of the invention.

The compounds of the invention may also contain one or more asymmetric carbon atoms and may therefore exhibit optical and/or diastereoisomerism. Diastereoisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. All stereoisomers are included within the scope of the invention.

Also included within the scope of the invention are radiolabelled derivatives of compounds of formulae IA and IB which are suitable for biological studies.

Preparation

According to a further aspect of the invention there is provided processes for the preparation of compounds of the invention, as illustrated below.

The following processes are illustrative of the general synthetic procedures which may be adopted in order to obtain the compounds of the invention:

1. Compounds of formulae IA and IB may be prepared by cyclisation of corresponding compounds of formulae IIA and IIB, respectively:

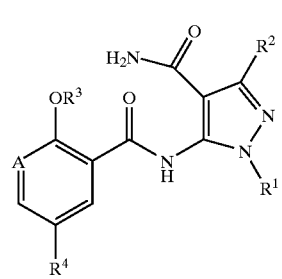

IIA

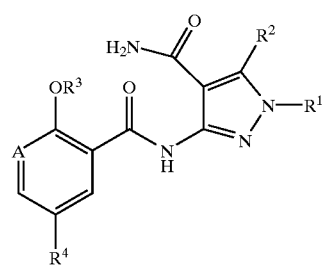

IIB wherein $R^1$, $R^2$, $R^3$, $R^4$ and A are as defined previously for compounds of formulae IA and IB.

This cyclisation may be accomplished under basic, neutral or acidic conditions using known methods for pyrimidone ring formation. Preferably, the cyclisation is performed under basic conditions using an alkali metal salt of an alcohol or amine, such as sodium ethoxide, potassium tert-butoxide or potassium bis(trimethylsilyl) amide, in the presence of a suitable solvent, for example at reflux temperature (or, if performed in a sealed vessel, at greater than reflux temperature). The skilled person will appreciate that, when an alcohol is selected as solvent, an appropriate alcohol of formula R³OH, or a sterically hindered alcohol, eg 3-methyl pentan-3-ol, may be used if it is intended to mitigate alkoxide exchange at either the 2-position of the pyridin-3-yl, or the phenyl, substituent.

Compounds of formulae IIA and IIB may be prepared by reaction of corresponding compounds of formulae IIIA and IIIB, respectively:

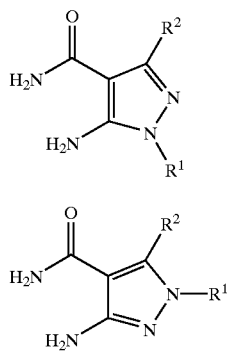

wherein R¹ and R² are as defined previously for compounds of formulae IIA and IIB, with a compound of formula IV or a carboxylic acid derivative thereof:

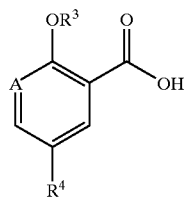

wherein R³, R⁴ and A are as defined previously for compounds of formula IIA and IIB.

This coupling reaction may be achieved by conventional amide bond forming techniques which are well known to those skilled in the art. For example, an acyl halide (e.g. chloride) derivative of a compound of formula IV may be reacted with a compound of formula IIIA or IIIB in the presence of an excess of a tertiary amine, such as triethylamine or pyridine, optionally in the presence of a suitable catalyst, such as 4-dimethyl aminopyridine, in a suitable solvent such as dichloromethane, at a temperature of about 0° C. to room temperature.

A variety of other amino acid coupling methodologies may be used to couple the compound of formula IIIA and IIIB with the compound of formula IV. For example, the acid of formula IV or a suitable salt thereof (eg sodium salt) may be activated with an appropriate activating reagent, e.g. a carbodiimide, such as 1,3-dicyclocarbodiimide or 1-(3-dimethylaminopropyl)-3-ethylcarbodiimide hydrochloride optionally in the presence of 1-hydroxybenzotriazole hydrate and/or a catalyst such as 4-dimethylaminopyridine; a halotrisaminophosphonium salt such as bromotris (pyrrolidinyl)phosphonium hexafluorophosphate; or a suitable pyridinium salt such as 2-chloro-1-methyl pyridinium chloride. Either type of coupling reaction may be conducted in a suitable solvent such as dichloromethane or tetrahydrofuran, optionally in the presence of a tertiary amine such as N-methylmorpholine or N-ethyldiisopropylamine (for example when either the compound of formula IIIA or IIIB, or the activating agent is presented in the form of an acid addition salt), at from about 0° C. to about room temperature. Preferably, from about 1 to 2 molecular equivalents of the activating reagent and from 1 to 3 molecular equivalents of any tertiary amine present may be employed.

Alternatively, the carboxylic acid function of IV may be activated using an excess of a reagent such as N,N'-carbonyldiimidazole in an appropriate solvent, eg ethyl acetate, dichloromethane or butan-2-one, at from about room temperature to about 80° C., followed by reaction of the intermediate imidazolide with either a compound of the formula IIIA or IIIB at from about 20° C. to about 90° C.

In a further variation, a compound of formula IA or IB, as defined previously, may be formed in a one-pot procedure by coupling a compound of formula IIIA or IIIB with the acyl chloride derivative of formula IV and by cyclising the resultant intermediate compound of formula IIA or IIB, using the methods as described previously. The one-pot procedure may further involve an in-situ coupling and cyclisation reaction to form a compound of formula IA or IB. Preferably, pyridine may serve as an acid scavenger and as the solvent for the in-situ coupling and cyclisation reaction.

2. Compounds of formulae IA and IB may be prepared by cyclisation of corresponding compounds of formulae VA and VB, respectively:

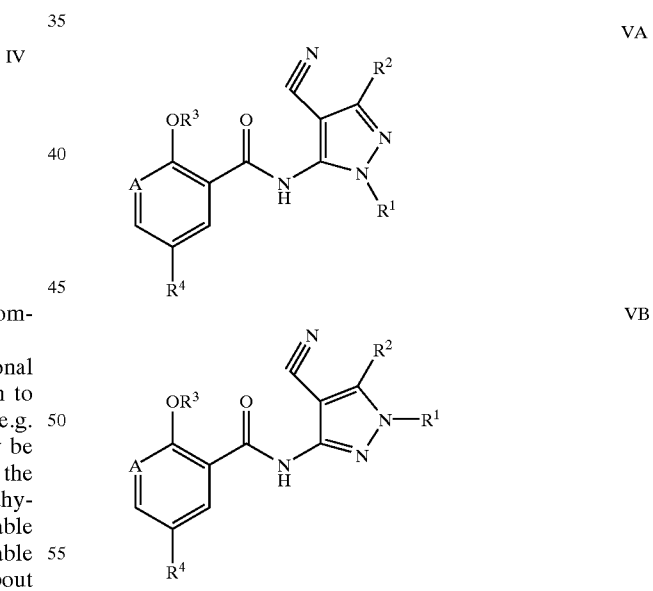

wherein R¹, R², R³, R⁴ and A are as defined previously for compounds of formulae IA and IB.

Preferably, the cyclisation is accomplished via hydrolysis, more preferably in the presence of a suitable base such as potassium hydroxide and a suitable solvent, such as a sterically hindered alcohol, such as 3-methyl-3-pentanol, for example at reflux temperature.

Compounds of formulae VA and VB may be prepared by reaction of corresponding compounds of formulae VIA and VIB, respectively:

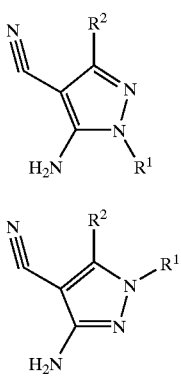

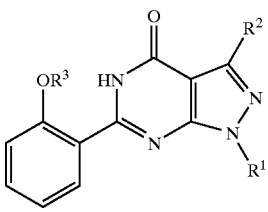

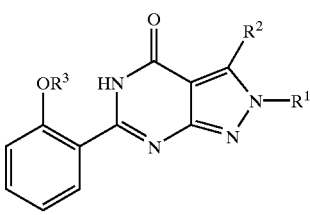

wherein $R^1$ and $R^2$ are as previously defined for compounds of formulae VA and VB, with a compound of formula IV or a carboxylic acid derivative thereof as defined previously, using standard amide bond forming techniques, for example as described hereinbefore in respect of the coupling of a compound of formula IIIA or IIIB with a compound of formula IV.

3. Compounds of formulae IA and IB may be prepared by reaction of corresponding compounds of formulae VIIA and VIIB, respectively:

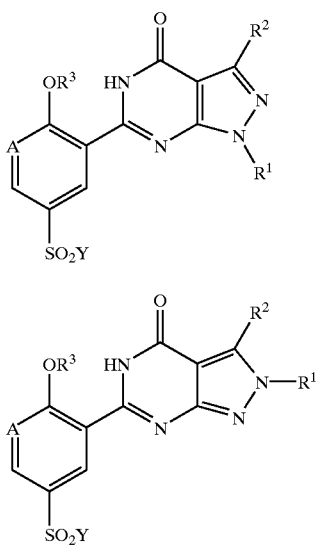

wherein Y is halo, preferably chloro, bromo or iodo, $R^1$, $R^2$, $R^3$ and A are as previously defined for compounds of formulae IA and IB, with a compound of formula VIII:

$$R^{12}R^{13}NH \qquad VIII$$

wherein $R^{12}$ and $R^{13}$ are as previously defined for compounds of formulae IA and IB.

This reaction is typically performed at 0° C. to room temperature, preferably in the presence of an appropriate solvent such as a $C_1$ to $C_3$ alcohol or dichloromethane, optionally using an excess of the compound of formula VIII and, optionally, in the presence of another suitable base, such as triethylamine.

Compounds of formulae VIIA and VIIB in which A is CH may be prepared from corresponding compounds of formulae IXA and IXB, respectively:

wherein $R^1$, $R^2$ and $R^3$ are as previously defined for compounds of formulae VIIA and VIIB, for example using conventional methods for the introduction of a $SO_2Y$ group into an aromatic ring system, for example reaction with a compound of formula $SO_2Y$ and/or a compound at formula $YSO_3H$. When Y is chloro, an excess of chlorosulphonic acid, optionally with an excess of thionyl chloride, at from about 0° C. to room temperature, may be used in an appropriate organic solvent (e.g. dichloromethane).

Compounds of formulae IXA and IXB in which $R^1$ represents lower alkyl, alkylHet or alkylaryl may be prepared by alkylation of a corresponding compound of formula X:

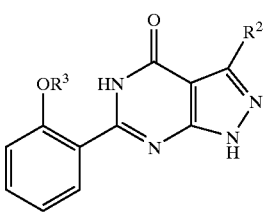

wherein $R^2$ and $R^3$ are as previously defined for compounds of formulae IXA and IXB, using methods which are well known to those skilled in the art, for example:

(i) reaction of a compound of formula X with a compound of formula $R^{1a}L^1$, wherein $R^{1a}$ represent lower alkyl, alkylHet or alkylaryl, and $L^1$ is a suitable leaving group, using conventional techniques which are well known to those skilled in the art. Preferably, the leaving group is halo (preferably chloro, bromo or iodo) and the alkylation is performed in the presence of an appropriate base, optionally in the presence of sodium iodide or potassium iodide, at from about −70° C. to about 100° C. Preferably the alkylation is conducted at from about room temperature to about 80° C.

Suitable base-solvent combinations may be selected from:

(a) sodium, potassium or cesium carbonate, sodium or potassium bicarbonate, or a tertiary amine such as triethylamine or pyridine, together with a $C_1$ to $C_4$ alkanol, 1,2-dimethoxyethane, tetrahydrofuran, 1,4-dioxan, acetonitrile, pyridine, dimethylformamide or N,N-dimethylacetamide;

(b) sodium or potassium hydroxide, or a sodium or potassium $C_1$ to $C_4$ alkoxide, together with a $C_1$ to $C_4$ alkanol, water or mixtures thereof;

(c) lithium, sodium or potassium hydride, lithium, sodium or potassium bis(trimethylsilyl)amide, lithium diisopropylamide or butyllithium, together with toluene, ether, 1,2-dimethoxyethane, tetrahydrofuran or 1,4-dioxan; or (d) under phase transfer catalysis conditions, a tetraalkylammonium halide or hydroxide, together with a mixture of an aqueous solution of sodium or potassium hydroxide and dichloromethane, 1,2-dichloroethane or chloroform;

(ii) reaction of a compound of formula X with a compound of formula $R^{1a}OH$, wherein $R^{1a}$ is as defined above. Typical reaction conditions involve treating X with the alkanol in the presence of a triarylphosphine and a di($C_1$ to $C_4$)alkyl azodicarboxylate, in a suitable solvent such as tetrahydrofuran or 1,4-dioxane, at from about −50° C. to about room temperature.

Compounds of formulae IXA and IXB, in which $R^2$ represents lower alkyl, alkylHet or alkylaryl, may be alternatively prepared from corresponding compounds of formulae XIA and XIB, respectively:

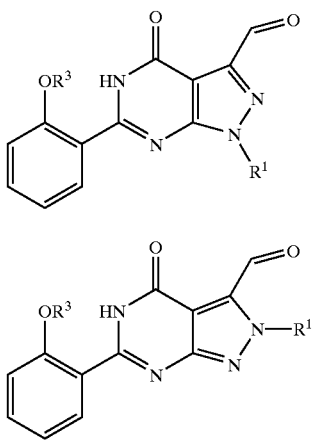

XIA

XIB wherein $R^1$ and $R^3$ are as previously defined for compounds of formulae IXA and IXB, by reaction with an organometallic compound of formula:

$R^{2a}M$ wherein M represents for example Li or MgHal, Hal represents halo (e.g. Br) and $R^{2a}$ represents a group which provides the relevant group $R^2$ upon reaction with the —C=O group which is attached to the pyrazole ring (e.g. when the $R^2$ group to be formed is ethyl, $R^{2a}$ represents methyl and when the $R^2$ group to be formed represents benzyl, $R^{2a}$ represents phenyl), followed by deoxygenation of the resultant secondary alcohol, using methods which are well known to those skilled in the art.

Compounds of formula $R^{2a}M$ are commercially available or are available using well known methods, for example, when M represents Li and $R^{2a}$ represents alkyl, by reacting an alkyl lithium reagent with a compound of the formula $R^{2a}Z$, wherein Z is a group that undergoes lithium exchange such as halo (eg bromo and iodo) or a tri-alkyl-stannyl group, in a suitable solvent such as tetrahydrofuran at low temperature, preferably below minus 68° C. (e.g. −78° C.).

Preferably, the compounds of formulae XIA and XIB are reacted with an excess of the reagent $R^{2a}M$, at low temperatures, preferably below −68° C. (e.g. −78° C.), in a suitable solvent such as tetrahydrofuran. Preferably, the alcohol functionality of the resultant secondary alcohol is converted to an alkyl group. For example by reaction with thiocarbonyldiimidazole followed by hydride reduction. Typically, the reduction of the derivatised secondary alcohol is effected with a hydrogen atom donor, such as with tri-n-butyltin hydride, in a suitable solvent, such as toluene, at reflux temperature of the reaction.

Compounds of formulae XIA and XIB may be prepared by the oxidation of corresponding compounds of formulae XIIA and XIIB, respectively:

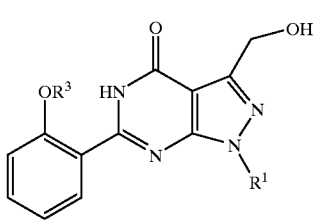

XIIA

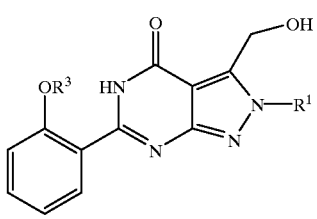

XIIB wherein $R^1$ and $R^3$ are as defined previously for compounds of formulae XIA and XIB, using methods which are well known to those skilled in the art.

Compounds of formulae XIIA and XIIB may be prepared by cyclising corresponding compounds of formulae XIIIA and XIIIB, respectively:

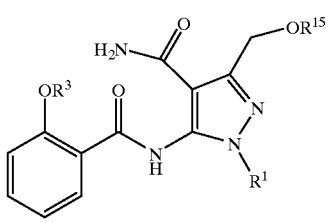

XIIIA

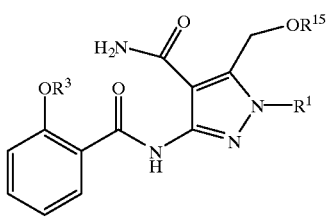

XIIIB wherein $R^1$ and $R^3$ are as defined previously for compounds of formulae XIIA and XIIB, and $R^{15}$ represents an alcohol protecting group, such as benzyl, which is stable to the conditions of the cyclisation reaction, and which may be removed under mild conditions which do not substantially affect the integrity of the resultant compound of formula XIIA or XIIB. The cyclisation reaction may be performed using analogous conditions to those previously described for compounds of formulae IIA and IIB.

Typically, the compounds of formulae XIIIA and XIIIB may be prepared by coupling compounds of the formulae XIVA and XIVB, respectively:

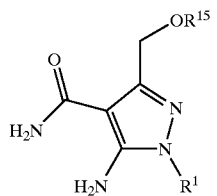

XIVA

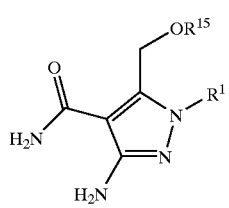

XIVB wherein $R^1$ and $R^{15}$ are as previously defined for compounds of formulae XIIIA and XIIIB, with a compound of the formula XV or a carboxylic acid derivative thereof:

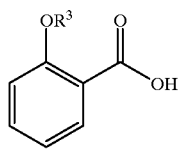

XV wherein $R^3$ is as previously defined for compounds of formulae XIIIA and XIIIB. The coupling reaction may be achieved by conventional amide bond forming techniques which are well known to those skilled in the art, for example, by using techniques which are analogous to those used to couple compounds of formulae IIIA or IIIB with a compound of formula IV.

Compounds of formulae VIIA and VIIB in which A represents N may be prepared from corresponding compounds of formulae XVA and XVB, respectively:

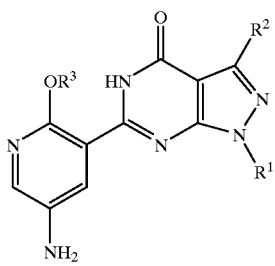

XVA

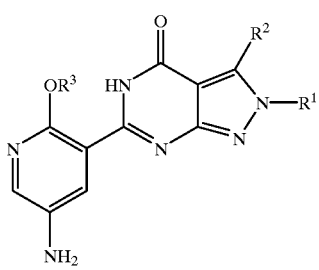

XVB wherein $R^1$, $R^2$ and $R^3$ are as previously defined for compounds of formulae VIIA and VIIB, for example using methods known to those skilled in the art for converting an amino group to an $SO_2Y$ group (in which Y is as previously defined for compounds of formulae VIIA and VIIB). For example, compounds of formulae VIIA and VIIB in which Y is chloro may be prepared by reacting a corresponding compound of formula XVA or XVB with about a two-fold excess of sodium nitrite in a mixture of concentrated hydrochloric acid and glacial acetic acid, at from about −25° C. to about 0° C., followed by treatment with excess liquid sulphur dioxide and a solution of about a three-fold excess of cupric chloride in aqueous acetic acid, at from about −15° C. to about room temperature.

Compounds of formula XVA and XVB may be prepared by cyclisation of a corresponding compound of formula XVC or XVD (as appropriate):

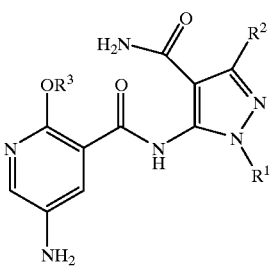

XVC

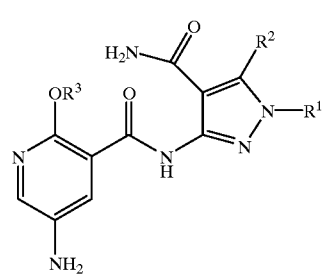

XVD wherein $R^1$, $R^2$ and $R^3$ are as hereinbefore defined for compounds of formulae XVA and XVB, for example under similar conditions to those described hereinbefore for preparation of compounds of formulae IA and IB.

Compounds of formulae XVA and XVB may alternatively be prepared by reduction of the corresponding nitropyridine compound under conditions which are well known to those skilled in the art. Such nitro compounds may be prepared by cyclisation of appropriate precursors, for example as described above.

4. Compounds of formulae IA and IB, in which $R^2$ represents lower alkyl, alkylHet or alkylaryl, may alternatively be prepared by reaction of corresponding compounds of formulae XVIA and formula XVIB, respectively:

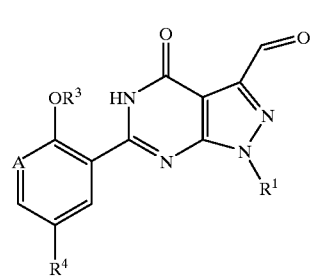

XVIA

XVIB

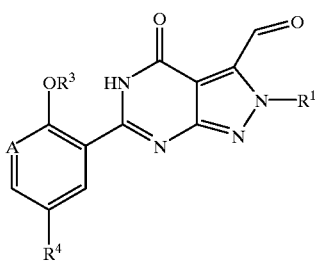

wherein $R^1$, $R^3$, $R^4$ and A are as previously defined for compounds of formulae IA and IB, with either an organometallic compound of formula $R^{2a}M$ as hereinbefore defined, followed by deoxygenation of the resultant secondary alcohol, using methods which are well known to those skilled in the art, or by reductive amination using a basic compound which provides an $R^2$ group upon reaction with the —C=O group which is attached to the pyrazole ring (e.g. a group which provides $(R^{2a})^-$, prior to reaction with the carbonyl, such a morpholinyl), using methods which are well known to those skilled in the art.

Compounds of formulae XVIA and XVIB may be prepared by oxidation of corresponding compounds of formulae IA or IB, in which $R^2$ represents $CH_2OH$ using methods which are well known to those skilled in the art.

5. Compounds of formulae IA and IB in which $R^2$ represents $CH_2OH$ may be prepared by the deprotection of corresponding compounds of formulae XVIIA and XVIIB, respectively:

XVIIA

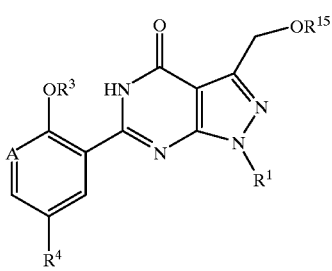

XVIIB

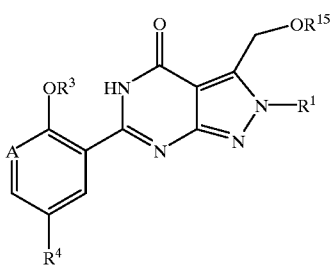

wherein $R^1$, $R^3$, $R^4$ and A are as previously defined for compounds of formulae IA and IB and $R^{15}$ represents an alcohol protecting group, for example a benzyl group, using methods that are well known to those skilled in the art. (It will be appreciated by those skilled in the art that compounds of formula XVIIA and XVIIB may also be compounds of the invention.)

6. Compounds of formulae IA and IB in which $R^1$ represents lower alkyl, alkylHet or alkylaryl may be prepared by alkylation of corresponding compounds of formulae IA and IB, respectively, in which $R^1$ represents H, for example as described hereinbefore for preparation of compounds of formulae IXA and IXB.

Compounds of formulae IIIA and IIIB, IV, VIA and VIB, VIII, X, XIVA and XIVB, XV, and XVC and XVD, and compounds of formulae $R^1L^1$, $R^{1a}OH$ and $R^{2a}Z$, and derivatives thereof, when not commercially available or not subsequently described, may be obtained either by analogy with the processes described herein, or by conventional synthetic procedures, in accordance with standard techniques, from readily accessible starting materials using appropriate reagents and reaction conditions.

Substituents on the aryl and Het groups in the above-mentioned compounds may be introduced, and interconverted, using techniques which are well known to those skilled in the art.

The skilled person will also appreciate that various standard substituent or functional group interconversions and transformations within certain compounds of formulae IA and IB will provide other compounds of formulae IA and IB. Examples include alkoxide exchange at the 2-position of the 5-phenyl and the pyridin-3-yl substituents, and for compounds in which $R^1$, $R^2$, $R^3$ and $R^4$ represents an alkyl group which is terminated by OH, deprotection of a corresponding ether compound of formula IA or IB (see the Examples below). Moreover, certain compounds of formulae IA and IB, for example those in which $R^{12}$ and $R^{13}$, together with the nitrogen to which they are attached, form a 4-$R^{14}$-piperazinyl group, in which $R^{14}$ does not represent H, may be prepared directly from the corresponding piperazine analogues in which $R^{14}$ is hydrogen, using standard procedures (e.g. alkylation).

The compounds of the invention may be isolated from their reaction mixtures using conventional techniques.

It will be appreciated by those skilled in the art that, in the course of carrying out the above processes described above, the functional groups of intermediate compounds may need to be protected by protecting groups.

Functional groups which it is desirable to protect include hydroxy, amino and carboxylic acid. Suitable protecting groups for hydroxy include trialkylsilyl and diarylalkylsilyl groups (e.g. tertbutyldimethylsilyl, tertbutyldiphenylsilyl or trimethylsilyl) and tetrahydropyranyl. Suitable protecting groups for amino include tertbutyloxycarbonyl, 9-fluorenylmethoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art.

The use of protecting groups is fully described in "Protective Groups in Organic Chemistry", edited by JWF McOmie, Plenum Press (1973), and "Protective Groups in Organic Synthesis", $2^{nd}$ edition, T W Greene & P G M Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Pharmaceutically acceptable acid addition salts of the compounds of formulae IA and IB which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formula IA or IB with the appropriate base. Both types of salt may be formed or interconverted using ion-exchange resin techniques.

It will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula I may act as prodrugs of other compounds of formula I.

All protected derivatives, and prodrugs, of compounds of formula I are included within the scope of the invention.

Medical Use

The compounds of the invention are useful because they possess pharmacological activity in animals, especially mammals, including humans. They are therefore indicated as pharmaceuticals, as well as for use as animal medicaments.

According to a further aspect of the invention there is provided the compounds of the invention for use as pharmaceuticals, and for use as animal medicaments.

In particular, compounds of the invention have been found to be potent and selective inhibitors of cGMP PDEs, such as cGMP PDE5, for example as demonstrated in the tests described below, and are thus useful in the treatment of medical conditions in humans, and in animals, in which cGMP PDEs, such as cGMP PDE5, are indicated, and in which inhibition of cGMP PDEs, such as cGMP PDE5, is desirable.

By the term "treatment", we include both therapeutic (curative) or prophylactic treatment.

Thus, according to a further aspect of the invention there is provided the use of the compounds of the invention in the manufacture of a medicament for the treatment of a medical condition in which a cGMP PDE (e.g. cGMP PDE5) is indicated. There is further provided the use of the compounds of the invention in the manufacture of a medicament for the treatment of a medical condition in which inhibition of a cGMP PDE (e.g. cGMP PDE5) is desirable.

The compounds of the invention are thus expected to be useful for the curative or prophylactic treatment of male erectile dysfunction (MED), female sexual dysfunction (FSD), premature labour, dysmenorrhoea, benign prostatic hyperplasia (BPH), bladder outlet obstruction, incontinence, stable and unstable variant (Prinzmetal) angina, hypertension, pulmonary hypertension, congestive heart failure, atherosclerosis, stroke, peripheral vascular disease, conditions of reduced blood vessel patency (e.g. post transluminal coronary angioplasty (post-PTCA)), chronic asthma, bronchitis, allergic asthma, allergic rhinitis, glaucoma and diseases characterised by disorders of gut motility (e.g. irritable bowel syndrome (IBS)). Other conditions which may be mentioned include pre-eclampsia, Kawasaki's syndrome, nitrate tolerance, multiple sclerosis, peripheral diabetic neuropathy, stroke, Alzheimer's disease, acute respiratory failure, psoriasis, skin necrosis, cancer metastasis, baldness, nutcracker oesophagus, anal fissure and hypoxic vasoconstriction. Particularly preferred conditions include MED and FSD.

Thus, the invention provides a method of treating or preventing a medical condition for which a cGMP PDE5 inhibitor is indicated, in an animal (e.g. a mammal, including a human being), which comprises administering a therapeutically effective amount of a compound of the invention to a mammal in need of such treatment.

Pharmaceutical Preparations

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds of the invention may also be combined with any other drugs useful in the inhibition of cGMP-PDEs, such as cGMP-PDE5.

In human therapy, the compounds of the invention can be administered alone but will generally be administered in admixture with a suitable pharmaceutical excipient diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention will usually be from 10 to 500 mg/kg (in single or divided doses).

Thus, for example, the tablets or capsules of the compound of the invention may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™ or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg, which may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The skilled person will also be appreciated that, in the treatment of certain conditions (including MED and FSD), compounds of the invention may be taken as a single dose on an "as required" basis (i.e. as needed or desired).

Generally, in humans, oral administration of the compounds of the invention is the preferred route, being the most convenient and, for example in MED, in avoiding the well-known disadvantages associated with intracavernosal (i.c.) administration.

A preferred oral dosing regimen in MED for a typical man is from 25 to 250 mg of compound when required.

In circumstances where the recipient suffers from a swallowing disorder or from impairment of drug absorption after oral administration, the drug may be administered parenterally, e.g. sublingually or bucally.

For veterinary use, a compound of the invention is administered as a suitably acceptable formulation in accordance with normal veterinary practice and the veterinary surgeon will determine the dosing regimen and route of administration which will be most appropriate for a particular animal.

Thus, according to a further aspect of the invention there is provided a pharmaceutical formulation including a compound of the invention in admixture with a pharmaceutically or veterinarily acceptable adjuvant, diluent or carrier.

In addition to the fact that compounds of the invention inhibit cyclic guanosine 3',5'-monophosphate phosphodiesterases (cGMP PDEs) and in particular, are potent and selective inhibitors of cGMP PDE5, compounds of the invention may also have the advantage that they may be more efficacious than, be less toxic than, have a broader range of activity than, be more potent than, produce fewer side effects than, be more easily absorbed than, or they may have other useful pharmacological properties over, compounds known in the prior art.

The biological activities of the compounds of the present invention were determined by the following test methods.

Biological Tests

Phosphodiesterase (PDE) Inhibitory Activity

In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (Ca/CAM)-dependent PDE (PDE1) from human cardiac ventricle; the cAMP-specific PDE (PDE4) from human skeletal muscle; and the photoreceptor PDE (PDE6) from bovine retina.

Assays were performed using a modification of the "batch" method of W. J. Thompson et al. (Biochem., 1979, 18, 5228). Results from these tests show that the compounds of the present invention are potent and selective inhibitors of cGMP-specific PDE5.

Functional Activity

This was assessed in vitro by determining the capacity of a compound of the invention to enhance sodium nitroprusside-induced relaxation of precontracted rabbit corpus cavernosum tissue strips, as described by S. A. Ballard et al. (Brit. J. Pharmacol., 1996, 118 (suppl.), abstract 153P).

In Vivo Activity

Compounds may be screened in anaesthetised dogs to determine their capacity, after i.v. administration, to enhance the pressure rises in the corpora cavernosa of the penis induced by intracavernosal injection of sodium nitroprusside, using a method based on that described by TrigoRocha et al. (Neurourol. and Urodyn., 1994, 13, 71).

Safety Profile

Compounds of the invention may be tested at varying i.v and p.o. doses in animals such as mouse and dog, observing for any untoward effects.

EXAMPLES AND PREPARATIONS

The synthesis of the compounds of the invention and of the intermediates for use therein are illustrated by the following Examples and Preparations.

$^1$H nuclear magnetic resonance (NMR) spectra were recorded using either a Varian Unity 300 or a Varian Inova 400 spectrometer and were in all cases consistent with the proposed structures. Characteristic chemical shifts ($\delta$) are given in parts-per-million downfield from tetramethylsilane using conventional abbreviations for designation of major peaks: eg s, singlet; d, doublet; t, triplet; q, quartet; m, multiplet; br, broad.

Mass spectra (m/z) were recorded using a Fisons Instruments Trio mass spectrometer in the thermospray ionisation mode.

Room temperature includes 20 to 25° C.

Synthesis of Intermediates

Preparation 1

2-(1-Hydroxy-2-phenylethylidene)malononitrile

A solution of malononitrile (4.0 g, 60 mmol) in tetrahydrofuran (25 ml), was added dropwise over an hour to an ice-cooled suspension of sodium hydride (4.80 g, 60%, 120 mmol) in tetrahydrofuran (75 ml), and the mixture stirred at room temperature for an hour, and then re-cooled to 0° C. A solution of phenylacetyl chloride (8.0 ml, 60 mmol) in tetrahydrofuran (20 ml) was added dropwise over an hour, maintaining the temperature below 10° C., and the reaction mixture then stirred at room temperature for 36 hours. Water (10 ml) was added, the mixture concentrated under reduced pressure, the residue partitioned between ether (50 ml), and 1N hydrochloric acid (50 ml) and the phases separated. The aqueous layer was extracted with ether (2×50 ml), the combined organic layers washed with brine (50 ml), dried ($Na_2SO_4$) and evaporated under reduced pressure. The residue was dissolved in acetonitrile (100 ml), filtered to remove residual silicon oil, and the filtrate evaporated under reduced pressure, to afford the title compound as a brown oil, (11.20 g).

$\delta$ ($CDCl_3$): 3.93 (2H, s), 7.30 (2H, m), 7.40 (3H, m).

Preparation 2

2-[2-(Benzyloxy)-1-hydroxyethylidene]malononitrile

Obtained as a beige solid (33%), after recrystallisation from diisopropyl ether, from benzyloxyacetyl chloride and malononitrile, using a similar procedure to that described in preparation 1.

$\delta$ ($CDCl_3$): 4.46 (2H, s), 4.72 (2H, s), 7.34 (2H, m), 7.41 (3H, m).

Preparation 3

2-(1-Hydroxy-2-methylpropylidene)malononitrile

Obtained as a beige solid (88%) from isobutyryl chloride and malononitrile using the procedure of preparation 1.

$\delta$ ($CDCl_3$): 1.23 (6H, d), 3.16 (1H, m).

Preparation 4

2-(2-Cyclobutyl-1-hydroxyethylidene)malononitrile

Obtained as a brown oil (100%) from cyclopropylacetyl chloride (J. Med. Chem. 1984, 27, 1291) and malononitrile, using the procedure of preparation 1.

$\delta$ ($CDCl_3$): 0.34 (2H, m), 0.63 (2H, m), 1.05 (1H, m), 2.53 (2H, d), 9.72 (1H, s). LRMS: m/z 166 $(M+18)^+$ Preparation 5

2-(1-Methoxy-2-phenylethylidene)malononitrile

A solution of the title compound of preparation 1 (11.20 g, 62 mmol) in tetrahydrofuran (50 ml) was added dropwise to an ice cooled solution of sodium hydride (5.86 g, 60%, 62 mmol) in tetrahydrofuran (40 ml) and the mixture stirred at room temperature for 20 minutes, then re-cooled to 0° C. in an ice bath. A solution of dimethyl sulphate (2.48 g, 62 mmol) in tetrahydrofuran (40 ml) was added dropwise over an hour and once addition was complete the reaction was heated under reflux for 3 hours, then stirred for a further 18 hours at room temperature. The reaction mixture was concentrated under reduced pressure, the residue partitioned between ethyl acetate (100 ml) and ice cold sodium hydrogen carbonate solution (50 ml), and the phases separated. The organic layer was washed with water (25 ml), brine (25 ml), dried ($Na_2SO_4$) and evaporated under reduced pressure. The residual oil was purified by column chromatography on silica gel, using an elution gradient of ether:pentane (95:5 to 50:50) to afford the title compound as an orange oil, (7.47 g).

$\delta$ ($CDCl_3$): 4.02 (5H, m), 7.22–7.42 (5H, m).

Preparation 6

2-[2-(Benzyloxy)-1-methoxyethylidene]malononitrile

Obtained as a brown oil (78%) from the title compound of preparation 2, using a similar procedure to that described in preparation 5.

$\delta$ ($CDCl_3$): 3.98 (3H, s), 4.20 (2H, s), 4.43 (2H, s), 7.38 (5H, m).

Preparation 7

2-(1-Methoxy-2-methylpropylidene)malononitrile

A solution of the title compound of preparation 3 (3.37 g, 24.8 mmol) in dioxan (25 ml) was added to a suspension of sodium hydride (780 mg, 26 mmol) in dioxan (40 ml), the mixture stirred for 10 minutes, and dimethyl sulphate (2.5 ml, 26 mmol) added dropwise. The reaction mixture was heated under reflux for 18 hours, cooled and concentrated under reduced pressure. The residue was partitioned between ethyl acetate (100 ml) and water (50 ml), the phases separated, and the organic layer washed with brine (25 ml), dried ($MgSO_4$) and evaporated under reduced pressure. The crude product was purified by column chromatography on silica gel, using dichloromethane as eluant to afford the title compound as a pale yellow oil, (2.62 g).

δ (CDCl$_3$): 1.20 (6H, d), 3.19 (1H, m), 4.38 (3H, s). LRMS: m/z 168 (M+18)$^+$

Preparation 8

2-(2-Cyclobutyl-1-methoxyethylidene)malononitrile

Obtained as an oil (45%) from the title compound of preparation 4, using a similar procedure to that described in preparation 5.

δ (CDCl$_3$): 0.38 (2H, m), 0.62 (2H, m), 0.98 (1H, m), 2.58 (2H, d), 4.17 (3H, s). LRMS: m/z 180 (M+18)$^+$.

Preparation 9

5-Amino-3-benzyl-1-n-propyl-1H-pyrazole-4-carbonitrile

A mixture of propyl hydrazine oxalate (5.0 g, 30 mmol) and sodium methoxide (3.46 g, 60 mmol) in methanol (50 ml) was stirred at room temperature for 2 hours. A solution of the title compound of preparation 5 (6.03 g, 30 mmol) in methanol (10 ml) was added dropwise, and the reaction mixture heated under reflux for 4 hours. The cooled mixture was concentrated under reduced pressure, the residue suspended in a dichloromethane:methanol (90:10) (100 ml) solution and filtered. The filtrate was evaporated under reduced pressure and the crude product purified by column chromatography on silica gel, using an elution gradient of dichloromethane:methanol (100:0 to 95:5) to afford the title compound as a yellow solid, (5.13 g).

δ (CDCl$_3$): 0.95 (3H, t), 1.80 (2H, m), 3.78 (2H, t), 4.20 (2H, s), 7.18–7.34 (5H, m). LRMS: m/z 241 (M+1)$^+$.

Preparation 10

5-Amino-3-(benzyloxy)methyl-1-n-propyl-1H-pyrazole-4-carbonitrile

Sodium methoxide (7.2 g, 132 mmol) was added portionwise to a suspension of propyl hydrazine hydrochloride (7.3 g, 66 mmol) in methanol (100 ml) and the mixture stirred for 10 minutes. A solution of the title compound of preparation 6 (15.0 g, 66 mmol) in methanol (50 ml) was added dropwise over an hour, and once addition was complete, the reaction mixture was heated under reflux for 4 hours, and a further 18 hours at room temperature. Water (2 ml) was added, the mixture concentrated under reduced pressure and the residue partitioned between ethyl acetate (100 ml), and brine (100 ml), and the phases separated. The aqueous layer was extracted with ethyl acetate (2×100 ml), the combined organic layers dried (Na$_2$SO$_4$) and evaporated under reduced pressure. The crude product was purified by column chromatography on silica gel, using an elution gradient of dichloromethane:methanol (98:2 to 94:6) to afford the title compound, (3.7 g).

δ (CDCl$_3$): 0.88 (3H, t), 1.80 (2H, m), 3.88 (2H, t), 4.50 (2H, s), 4.55 (2H, s), 7.36 (5H, m). LRMS: m/z 271 (M+1)$^+$.

Preparation 11

5-Amino-3-(benzyloxy)methyl-1-ethyl-1H-pyrazole-4-carbonitrile

Obtained as a pale yellow oil (37%) from the title compound of preparation 6, and ethyl hydrazine oxalate using the procedure of preparation 10.

LRMS: m/z 258 (M+1)$^+$.

Preparation 12

5-Amino-3-isopropyl-1-n-propyl-1H-pyrazole-4-carbonitrile

Obtained as a yellow powder (6%) from the title compound of preparation 7 and propyl hydrazine hydrochloride, using the procedure of preparation 10.

δ (CDCl$_3$): 0.97 (3H, t), 1.32 (6H, d), 1.82 (2H, m), 2.98 (1H, m), 3.80 (2H, t), 4.10 (2H, s).

Preparation 13

5-Amino-3-cyclopropylmethyl-1-n-propyl-1H-pyrazole-4-carbonitrile

Obtained as a yellow solid (40%) from the title compound of preparation 8 and propyl hydrazine oxalate, using the procedure of preparation 9.

δ (CDCl$_3$): 0.22 (2H, m), 0.50 (2H, m), 0.92 (3H, t), 1.02 (1H, m), 1.80 (2H, m), 2.47 (2H, d), 3.78 (2H, t), 4.10 (2H, s). LRMS: m/z 205 (M+1)$^+$.

Preparation 14

5-Amino-1-ethyl-3-(2-pyrazinyl)-1H-pyrazole-4-carbonitrile

Sodium hydride (9.72 g, 60%, 243 mmol) was added portionwise to a cooled (5° C.) solution of malononitrile (7.9 g, 120 mmol) in tetrahydrofuran (75 ml), and the mixture stirred for 20 minutes. A solution of 2-pyrazinecarbonyl chloride (J. Med. Chem. 1992, 35, 1214) (17.1 g, 120 mmol) in tetrahydrofuran (250 ml) was added dropwise so as to maintain the internal temperature below 10° C., and the mixture then stirred at room temperature for an hour. Dimethyl sulphate (18.16 g, 144 mmol) was added, the mixture heated under reflux for 3 hours, allowed to cool, triethylamine (58.5 ml, 420 mmol) and ethyl hydrazine oxalate (18 g, 120 mmol) added and the reaction mixture heated under reflux for 18 hours. The solvent was decanted from the cooled reaction mixture and the residual brown gum extracted with dichloromethane (2×150 ml). The combined organic solutions were evaporated under reduced pressure and the crude product purified by column chromatography on silica gel, using ethyl acetate:hexane (50:50) as eluant to afford the title compound, (1.2 g).

δ (CDCl$_3$): 1.48 (3H, t), 4.03 (2H, q), 4.35 (2H, s), 8.50 (1H, s), 8.61 (1H, s), 9.17 (1H, s). LRMS: m/z 215 (M+1)$^+$.

Preparation 15

5-Amino-1-n-propyl-3-(2-pyrazinyl)-1H-pyrazole-4-carbonitrile

Obtained as a solid (5%) from malononitrile, propyl hydrazine hydrochloride and 2-(2-pyrazinyl)acetyl chloride, using a similar procedure to that described in preparation 14.

δ (CDCl$_3$): 1.02 (3H, t), 1.94 (2H, m), 3.97 (2H, t), 4.37 (2H, s), 8.55 (1H, s), 8.65 (1H, s), 9.20 (1H, s). LRMS: m/z 229 (M+1)$^+$.

Preparation 16

5-Amino-1-ethyl-3-phenyl-1H-pyrazole-4-carbonitrile

Obtained (23%) from benzoyl chloride, malononitrile and ethyl hydrazine oxalate using a similar procedure to that described in preparation 14.

δ (CDCl$_3$): 1.42 (3H, t), 3.98 (2H, q), 4.22 (2H, s), 7.37 (3H, m), 7.87 (2H, d). LRMS: m/z 213 (M+1)$^+$.

Preparation 17

5-Amino-3-benzyl-1-n-propyl-1H-pyrazole-4-carbonitrile

A mixture of the title compound of preparation 9 (1.80 g, 7.50 mmol) and sodium hydroxide (900 mg, 22.5 mmol) in ethanol (15 ml) and water (15 ml), was heated under reflux for 24 hours. The cooled reaction mixture was filtered and the solid dried under suction to afford the title compound as a white solid, (1.18 g).

δ (DMSOd$_6$): 0.86 (3H, t), 1.68 (2H, m), 3.80 (2H, t), 4.02 (2H, s), 6.18 (2H, s), 6.33 (2H, s), 7.18 (3H, m), 7.26 (2H, m). LRMS: m/z 259 (M+1)$^+$.

Preparation 18

5-Amino-3-(benzyloxy)methyl-1-ethyl-1H-pyrazole-4-carboxamide

Obtained as a solid (77%) from the title compound of preparation 11, using the procedure of preparation 17.
LRMS: m/z 275 (M+1)$^+$.

Preparation 19

5-Amino-3-(benzyloxy)methyl-1-n-propyl-1H-pyrazole-4-carboxamide

Obtained as white crystals (90%), from the title compound of preparation 10, using the procedure of preparation 17.

δ (CDCl$_3$): 0.84 (3H, t), 1.75 (2H, m), 3.80 (2H, t), 4.58 (2H, s), 4.63 (2H, s), 4.85 (2H, s), 7.34 (5H, m).

Preparation 20

5-Amino-3-isopropyl-1-n-propyl-1H-pyrazole-4-carboxamide

A mixture of the title compound of preparation 12 (834 mg, 4.3 mmol) and aqueous sodium hydroxide (13 ml, 1N, 13 mmol) in ethanol (15 ml) was heated under reflux for 72 hours. The cooled reaction mixture was partitioned between ethyl acetate (20 ml) and water (15 ml) and the phases separated. The aqueous layer was acidified to pH 6 with 2N hydrochloric acid and extracted with ethyl acetate (3×20 ml). These combined organic extracts were washed with brine, dried (MgSO$_4$) and evaporated under reduced pressure. The residual yellow oil was purified by column chromatography on silica gel, using an elution gradient of ether:hexane (35:65 to 100:0) to afford the title compound as a pale yellow solid, (260 mg).

δ (CDCl$_3$): 0.98 (3H, t), 1.37 (6H, d), 1.81 (2H, m), 2.99 (1H, m), 3.80 (2H, t), 5.29 (2H, s), 5.37 (2H, s). LRMS: m/z 211 (M+1)$^+$.

Preparation 21

5-Amino-3-cyclobutylmethyl-1-n-propyl-1H-pyrazole-4-carboxamide

Obtained as a solid (42%) from the title compound of preparation 13, using a similar procedure to that described in preparation 20, but using an elution gradient of dichloromethane:isopropanol (100:0 to 90:10).

δ (CDCl$_3$): 0.21 (2H, m), 0.50 (2H, m), 0.92 (3H, t), 1.04 (1H, m), 1.78 (2H, m), 2.70 (2H, d), 3.77 (2H, t), 5.23 (2H, s), 5.50 (2H, s). LRMS: m/z 223 (M+1)$^+$.

Preparation 22

5-Amino-1-ethyl-3-(2-pyrazinyl)-1H-pyrazole-4-carboxamide

A mixture of the title compound of preparation 14 (1.1 g, 5.1 mmol) and sodium hydroxide (617 mg, 15.4 mmol) in water (10 ml) and ethanol (10 ml) was heated under reflux for 24 hours and the cooled reaction mixture evaporated under reduced pressure. The residue was purified by column chromatography on silica gel, using an elution gradient of ethyl acetate:hexane:ethanol (50:50:0 to 90:0:10) to afford the title compound as a white solid, (695 mg).

δ (CDCl$_3$): 1.49 (3H, t), 4.02 (2H, q), 5.44 (1H, s), 5.74 (2H, s), 8.42 (1H, s), 8.55 (1H, s), 9.50 (1H, s), 10.43 (1H, s). LRMS: m/z 233 (M+1)$^+$.

Preparation 23

5-Amino-1-n-propyl-3-(2-pyrazinyl)-1H-pyrazole-4-carboxamide

Obtained as a solid (38%) from the title compound of preparation 15, using the procedure of preparation 22.

δ (CDCl$_3$): 1.01 (3H, t), 1.94 (2H, m), 3.96 (2H, t), 5.42 (1H, s), 5.70 (2H, s), 8.42 (1H, s), 8.55 (1H, s), 9.48 (1H, s), 10.44 (1H, s). LRMS: m/z 247 (M+1)$^+$.

Preparation 24

5-Amino-1-ethyl-3-phenyl-1H-pyrazole-4-carboxamide

A mixture of the title compound of preparation 16 (1.75 g, 8.3 mmol) and sodium hydroxide (990 mg, 24.8 mmol) in water (25 ml) and ethanol (25 ml) was heated under reflux for 24 hours. The cooled reaction mixture was concentrated under reduced pressure to remove the ethanol, and the residual aqueous solution extracted with dichloromethane (3×25 ml). The combined organic extracts were dried (Na$_2$SO$_4$) and evaporated under reduced pressure. The residue was purified by column chromatography on silica gel, using an elution gradient of ethyl acetate:hexane (50:50 to 100:0) to afford the title compound, (460 mg).

δ (CDCl$_3$): 1.40 (3H, t), 3.96 (2H, q), 5.15 (2H, s), 5.37 (2H, s), 7.41 (3H, m), 7.52 (2H, d). LRMS: m/z 231 (M+1)$^+$.

Preparation 25

3-[(Benzyloxy)methyl]-5-(2-n-propoxybenzamido)-1-n-propyl-1H-pyrazole-4-carboxamide A solution of 2-n-propoxybenzoyl chloride (1.98 g, 10 mmol) in dichloromethane (30 ml) was added to a cooled solution of the title compound of preparation 19 (2.88 g, 10 mmol) and triethylamine (2.02 g, 20 mmol) in dichloromethane (30 ml) and the reaction stirred for 90 minutes. The reaction mixture was concentrated under reduced pressure, the residue suspended in ethyl acetate (200 ml), washed consecutively with water (50 ml), 2N sodium hydroxide solution (50 ml), 2N hydrochloric acid (50 ml) and brine (50 ml), dried (MgSO$_4$) and evaporated under reduced pressure. The residue was purified by column chromatography on silica gel, using an elution gradient of hexane:ethyl acetate (100:0 to 0:100) to afford the title compound as a white solid, (3.17 g).

δ (CDCl$_3$): 0.84 (3H, t), 1.00 (3H, t), 1.80 (2H, m), 1.94 (2H, m), 4.00 (2H, t), 4.19 (2H, t), 4.58 (2H, s), 4.75 (2H, s), 6.98 (1H, d), 7.02 (1H, m), 7.32 (5H, m), 7.41 (1H, m), 8.21 (1H, d), 10.87 (1H, s).

Preparation 26

3-[(Benzyloxy)methyl]-6-(2-n-propoxyphenyl)-1-n-propyl-1,5-dihydro-4H-pyrazolo[3,4-d]pyrimidin-4-one A mixture of the title compound of preparation 25 (2.93 g, 6.5 mmol) and potassium t-butoxide (900 mg, 8.0 mmol) in isopropanol (50 ml) was heated under reflux for 5 hours, then cooled. The reaction mixture was diluted with ethyl acetate (100 ml), washed with ammonium chloride solution (50 ml) and brine (50 ml), dried ($MgSO_4$) and evaporated under reduced pressure. The residue was recrystallised from ether, to afford the title compound, (2.90 g).

δ ($CDCl_3$): 0.92 (3H, t), 1.16 (3H, t), 1.98 (4H, m), 4.17 (2H, t), 4.22 (2H, t), 4.58 (2H, s), 5.01 (2H, s), 7.00 (1H, d), 7.10 (1H, m), 7.29 (5H, m), 7.44 (1H, m), 8.60 (1H, d), 10.96 (1H, s).

Preparation 27

3-Methyl-6-(2-n-propoxyphenyl)-1H-1,5-dihydro-4H-pyrazolo[3,4-d]pyrimidin-4-one 2-n-Propoxybenzoyl chloride (12.2 g, 61 mmol) was added slowly to an ice cold suspension of 5-amino-4-cyano-3-methyl-1H-pyrazole (J. Med. Chem. 1996, 39, 1639) (5.0 g, 41 mmol) in pyridine (20 ml) and the reaction stirred at room temperature for an hour. Water (3 ml) was added, the mixture concentrated under reduced pressure and the residue partitioned between water (20 ml) and ethyl acetate (50 ml). The phases were separated, the organic layer dried ($Na_2SO_4$) and evaporated under reduced pressure and azeotroped with toluene to give a yellow solid. 30% Sodium peroxide solution (32 ml) was added slowly to a mixture of the intermediate amide, and sodium hydroxide solution (400 ml, 1N, 400 mmol) in ethanol (300 ml) and the reaction heated under reflux for 18 hours. The cooled reaction mixture was concentrated under reduced pressure, the residual aqueous solution acidified to pH 6 using hydrochloric acid, and the resulting precipitate filtered, washed with water and ether and dried under suction. This beige solid was purified by column chromatography on silica gel, using an elution gradient of ethyl acetate:hexane (20:80 to 50:50) and recrystallised from methanol to afford the title compound, (2.0 g).

δ ($CDCl_3$): 1.18 (3H, t), 2.02 (2H, m), 2.64 (3H, s), 4.20 (2H, t), 7.06 (1H, d), 7.26 (1H, m), 7.52 (1H, m), 8.43 (1H, d), 10.06 (1H, s), 11.08 (1H, s). LRMS: m/z 285 (M+1)$^+$.

Preparation 28

3-Methyl-6-(2-n-propoxyphenyl)-1-(pyridin-2-yl)methyl-1,5-dihydro-4H-pyrazolo[3,4-d]pyrimidin-4-one and

Preparation 29

3-Methyl-6-(2-n-propoxyphenyl)-2-(pyridin-2-yl)methyl-2,5-dihydro-4H-pyrazolo[3,4-d]pyrimidin-4-one Sodium hydride (78 mg, 60%, 2.6 mmol) was added to an ice cooled solution of the title compound of preparation 27 (205 mg, 0.7 mmol) in tetrahydrofuran (15 ml) and the mixture stirred for 30 minutes. 2-Chloromethyl pyridine (prepared from 576 mg, 2.2 mmol of the hydrochloride) in tetrahydrofuran (5 ml) was added and the reaction stirred at 50° C. for 48 hours and a further 72 hours at room temperature. Methanol (2 ml) was added and the reaction mixture evaporated under reduced pressure. The residue was purified by column chromatography on silica gel, using an elution gradient of hexane:isopropanol:0.88 ammonia (90:10:0.75 to 80:20:1.5) and repeated using ethyl acetate-:hexane (80:20 to 100:0) to afford the title compound of preparation 28, (85 mg).

δ ($CDCl_3$): 1.20 (3H, t), 2.02 (2H, m), 2.63 (3H, s), 4.20 (2H, t), 5.70 (2H, s), 6.99–7.20 (4H, m), 7.48 (1H, m), 7.60 (1H, m), 8.46 (1H, d), 8.60 (1H, s), 11.10 (1H, s). LRMS: m/z 376 (M+1)$^+$.

followed by the title compound of preparation 29, (210 mg).

δ ($CDCl_3$): 1.14 (3H, t), 1.98 (2H, m), 2.69 (3H, s), 4.16 (2H, t), 5.50 (2H, s), 6.99–7.20 (4H, m), 7.42 (1H, m), 7.60 (1H, m), 8.54 (1H, d), 8.58 (1H, d), 10.85 (1H, d). LRMS: m/z 376 (M+1)$^+$.

Preparation 30

3-Methyl-6-(2-n-propoxyphenyl)-2-(pyrimidin-2-yl)-2,5-dihydro-4H-pyrazolo[3,4-d]pyrimidin-4-one Obtained as a solid (39%) from the title compound of preparation 27 and 2-bromopyrimidine, using a similar procedure to that described in preparation 29, but using ethyl acetate:hexane:ethanol (50:50:0 to 95:0:5)as chromatographic eluant.

δ ($CDCl_3$): 1.18 (3H, t), 2.00 (2H, m), 3.13 (3H, s), 4.18 (2H, t), 7.02 (1H, d), 7.12 (1H, m), 7.30 (1H, m), 7.46 (1H, m), 8.62 (1H, d), 8.85 (2H, d), 10.91 (1H, s). LRMS: m/z 363 (M+1)$^+$.

Preparation 31

3-Hydroxymethyl-6-(2-n-propoxyphenyl)-1-n-propyl-1,5-dihydro-4H-pyrazolo[3,4-d]pyrimidin-4-one A mixture of the title compound of preparation 26 (1.19 g, 2.75 mmol) and 10% palladium on charcoal (1.0 g) in industrial methylated spirits (IMS; 40 ml) was hydrogenated at 50 psi and 50° C. for 72 hours. The reaction mixture was filtered, the filter pad washed well with IMS and the combined filtrate evaporated under reduced pressure. The residue was purified by column chromatography on silica gel, using an elution gradient of ethyl acetate:hexane (0:100 to 100:0) to afford the title compound as a white solid (615 mg).

δ ($CDCl_3$): 0.94 (3H, t), 1.16 (3H, t), 1.98 (4H, m), 4.16 (4H, m), 4.94 (2H, d), 5.62 (1H, m), 7.02 (1H, d), 7.12 (1H, m), 7.45 (1H, m), 8.60 (1H, d), 11.14 (1H, s).

Preparation 32

4-Oxo-6-(2-n-propoxyphenyl)-1-n-propyl-1,5-dihydro-4H-pyrazolo[3,4-d]pyrimidine-3-carbaldehyde N-Methylmorpholine oxide (390 mg, 3.33 mmol), followed by tetrapropylammonium perruthenate (30 mg; 0.09 mmol) were added to a mixture of the title compound of preparation 31 (569 mg, 1.66 mmol) and 4Å molecular sieves (750 mg) in acetonitrile (10 ml) and dichloromethane (10 ml), and the reaction stirred at room temperature for 18 hours. The reaction mixture was filtered, the filtrate diluted with ethyl acetate (50 ml), washed with 0.5N hydrochloric acid (20 ml), then brine (20 ml), dried ($MgSO_4$) and evaporated under reduced pressure. The residue was purified by column chromatography on silica gel, using ethyl acetate as eluant, to afford the title compound as a white crystalline solid, (367 mg).

δ (CDCl$_3$): 0.98 (3H, t), 1.20 (3H, t), 2.00 (4H, m), 4.22 (2H, t), 4.70 (2H, t), 7.06 (1H, d), 7.18 (1H, m), 7.51 (1H, m), 8.62 (1H, d), 10.48 (1H, s), 11.30 (1H, s).

Preparation 33

3-[Hydroxy-(pyridin-2-yl)methyl]-6-(2-n-propoxyphenyl)-1-n-propyl-1,5-dihydro-4H-pyrazolo[3,4-d]pyrimidin-4-one n-Butyl lithium (2.5 ml, 1.6M in hexane, 4 mmol) was added dropwise to a cooled (−78° C.) solution of 2-bromopyridine (632 mg, 4 mmol) in tetrahydrofuran (10 ml) and the mixture stirred for 10 minutes. A solution of the title compound of preparation 32 (340 mg, 1 mmol) in tetrahydrofuran (5 ml) was added and the reaction stirred for 30 minutes. 2N hydrochloric acid (4 ml) was added, the mixture allowed to warm to room temperature, basified with 2N sodium hydroxide solution, and extracted with ethyl acetate (3×20 ml). The combined organic extracts were washed with brine (20 ml), dried (MgSO$_4$) and evaporated under reduced pressure. The residue was purified by column chromatography on silica gel, using an elution gradient of hexane:ethyl acetate (100:0 to 0:100) to afford the title compound as an oil, (246 mg).

δ (CDCl$_3$): 0.93 (3H, t), 1.14 (3H, t), 1.21 (1H, d), 1.98 (4H, m), 4.13 (2H, m), 4.34 (1H, m), 4.49 (1H, m), 6.18 (1H, d), 6.97–7.24 (3H, m), 7.41 (1H, m), 7.64 (2H, m), 8.41 (1H, s), 8.59 (1H, m), 11.15 (1H, s). LRMS: m/z 420 (M+1)$^+$.

Preparation 34

3-[Hydroxy-(pyrimidin-2-yl)methyl]-6-(2-n-propoxyphenyl)-1-n-propyl-1,5-dihydro-4H-pyrazolo[3,4-d]pyrimidin-4-one n-Butyl lithium (6.6 ml, 2.5M in hexane, 16.5 mmol) was added dropwise to a cooled (−78° C.) solution of tri-n-butyl-stannyl-2-pyrimidine (Tetrahedron, 1994, 50, 275) (6.06 g, 16.4 mmol) in tetrahydrofuran (50 ml), so as to maintain the internal temperature below −68° C., and the mixture stirred for 15 minutes. A solution of the title compound of preparation 32 (1.86 g, 5.47 mmol) in tetrahydrofuran (50 ml) was added dropwise over 20 minutes, and the reaction stirred for a further 30 minutes. Saturated ammonium chloride solution (50 ml) was added, the mixture allowed to warm to room temperature, and diluted with ethyl acetate (100 ml). The layers were separated, the organic layer washed with brine (50 ml), dried (MgSO$_4$), and evaporated under reduced pressure. The residue was purified by column chromatography on silica gel, using an elution gradient of dichloromethane:methanol (100:0 to 95:5) and triturated with ether, to afford the title compound as a crystalline solid, (450 mg).

δ (CDCl$_3$): 0.92 (3H, t), 1.14 (3H, t), 1.98 (4H, m), 4.16 (2H, t), 4.28 (1H, m), 4.45 (1H, m), 6.21 (1H, d), 7.00 (1H, d), 7.08 (1H, m), 7.18 (1H, m), 7.32 (1H, d), 7.43 (1H, m), 8.60 (1H, d), 8.70 (1H, s), 11.14 (1H, s). LRMS: m/z 421 (M+1)$^+$.

Preparation 35

O-[[4-oxo-6-(2-n-propoxyphenyl)-1-n-propyl-1,5-dihydro-4H-pyrazolo[3,4-d]pyrimidin-3-yl](2-pyridinyl)methyl]1H-imidazole-1-carbothioate A mixture of the title compound of preparation 33 (210 mg, 0.5 mmol), and thiocarbonyldiimidazole (534 mg, 3 mmol) in dichloromethane (10 ml) was stirred at room temperature for 5 days. The reaction mixture was purified directly by column chromatography on silica gel, using an elution gradient of hexane:ethyl acetate (100:0 to 0:100) to afford the title compound, (180 mg).

δ (CDCl$_3$): 1.00 (3H, t), 1.16 (3H, t), 1.95–2.16 (4H, m), 4.18 (2H, t), 4.60 (2H, m), 7.07 (4H, m), 7.46 (1H, m), 7.77 (1H, m), 7.93 (1H, s), 7.99 (1H, d), 8.10 (1H, s), 8.52–8.68 (3H, m), 10.98 (1H, s).

Preparation 36

O-[[4-oxo-6-(2-n-propoxyphenyl)-1-n-propyl-1,5-dihydro-4H-pyrazolo[3,4-d]pyrimidin-3-yl](2-pyrimidinyl)methyl]1H-imidazole-1-carbothioate A mixture of the title compound of preparation 34 (420 mg, 1.0 mmol) and thiocarbonyldiimidazole (890 mg, 5.0 mmol) in dichloromethane (10 ml) was stirred at room temperature for 24 hours. The reaction mixture was poured into water (20 ml), the layers separated, and the aqueous phase extracted with dichloromethane (3×40 ml). The combined organic extracts were dried (MgSO$_4$) and evaporated under reduced pressure. The residue was purified by column chromatography on silica gel, using an elution gradient of hexane:ethyl acetate (100:0 to 0:100) to afford the title compound as a yellow oil, (469 mg).

δ (CDCl$_3$): 0.84 (3H, t), 1.12 (3H, t), 1.97 (4H, m), 4.11 (2H, t), 4.38 (2H, t), 6.99–7.10 (4H, m), 7.25 (1H, m), 7.42 (1H, m), 7.78 (1H, s), 8.37 (1H, s), 8.60 (1H, d), 8.72 (2H, m), 10.99 (1H, s). LRMS: m/z 531 (M+1)$^+$.

Preparation 37

6-(2-n-Propoxyphenyl)-1-n-propyl-3-(pyridin-2-yl)methyl-1,5-dihydro-4H-pyrazolo[3,4-d]pyrimidin-4-one A solution of the title compound of preparation 35 (180 mg, 0.34 mmol) in toluene (10 ml) was added dropwise to a solution of tri-n-butyltin hydride (291 mg, 1 mmol) in toluene (10 ml) under reflux, over 30 minutes and the reaction heated for a further 3 hours under reflux. The cooled reaction mixture was purified directly by column chromatography on silica gel, using an elution gradient of hexane:ethyl acetate (100:0 to 0:100) to afford the title compound as a yellow gum, (32 mg).

δ (CDCl$_3$): 0.84 (3H, t), 1.14 (3H, t), 1.84 (2H, m), 1.98 (2H, m), 4.15 (2H, t), 4.25 (2H, t), 4.63 (2H, s), 7.00 (1H, d), 7.10 (2H, m), 7.40 (2H, m), 7.57 (1H, m), 8.45 (1H, d), 8.60 (1H, d), 10.98 (1H, s). LRMS: m/z 404 (M+1)$^+$.

Preparation 38

6-(2-n-Propoxyphenyl)-1-n-propyl-3-(pyrimidin-2-yl)methyl-1,5-dihydro-4H-pyrazolo[3,4-d]pyrimidin-4-one Obtained (32%) from the title compound of preparation 36, using a similar procedure to that described in preparation 37, except that an elution gradient of dichloromethane:methanol (100:0 to 96:4) was used as chromatographic eluant.

δ (CDCl$_3$): 0.81 (3H, t), 1.12 (3H, t), 1.84 (2H, m), 1.94 (2H, m), 4.12 (4H, m), 4.83 (2H, s), 6.99 (1H, d), 7.06 (1H, m), 7.13 (1H, m), 7.40 (1H, m), 8.59 (1H, d), 8.62 (2H, m), 10.85 (1H, s). LRMS: m/z 405 (M+1)$^+$.

Preparation 39

2-Ethoxy-5-[4-(2-hydroxymethyl)piperazin-1-ylsulphonyl]benzoic Acid

N-(2-hydroxyethyl)piperazine (3.40 ml, 28.0 mmol) was added to a solution of 2-ethoxy-5-chlorosulphonyl-benzoic acid (EP 812845 A1) (3.67 g, 14.0 mmol) in ethanol (25 ml) and the reaction mixture stirred at room temperature for 72 hours. The reaction mixture was concentrated under reduced pressure, the residue suspended in water, acidified to pH 6, and extracted with dichloromethane (3×50 ml). The combined organic extracts were dried ($Na_2SO_4$) and evaporated under reduced pressure. The residual brown oil was purified by column chromatography on reverse phase polystyrene resin using an elution gradient of water:acetonitrile (100:0 to 80:20) then triturated with acetonitrile to afford the title compound as a white solid, (1.10 g).

δ ($DMSOd_6$): 1.37 (3H, t), 2.38 (2H, t), 2.48 (4H, m), 2.84 (4H, m), 3.42 (2H, t), 4.20 (2H, q), 7.35 (1H, d), 7.80 (1H, d), 7.88 (1H, s). LRMS: m/z 359 (M+1)$^+$.

Preparation 40

2-Ethoxy-5-(4-methylpiperazin-1-ylsulphonyl) benzoic Acid Chloride Hydrochloride Oxalyl chloride (11.7 ml, 134 mmol) was added dropwise to an ice cold suspension of 2-ethoxy-5-(4-methylpiperazin-1-ylsulphonyl)benzoic acid (EP 812845 A1) (20.0 g, 60.9 mmol) and dimethylformamide (2 drops) in dichloromethane (200 ml) over 15 minutes, and the reaction mixture stirred at room temperature for 18 hours. The mixture was concentrated under reduced pressure, the residue triturated with ether then ethyl acetate and dried at 40° C. for 16 hours, to afford the title compound, (19.6 g).

δ ($DMSOd_6$): 1.35 (3H, t), 2.70 (5H, m), 3.12 (2H, m), 3.41 (2H, m), 3.75 (2H, m), 4.21 (2H, q), 7.38 (1H, d), 7.83 (1H, d), 7.94 (1H, s), 11.26 (1H, s).

Preparation 41

2-Ethoxy-5-[4-(2-hydroxyethyl)piperazin-1-ylsulphonyl]benzoic Acid Chloride Hydrochloride Oxalyl chloride (340 ml, 2.79 mmol) was added dropwise to an ice cold suspension of the title compound of preparation 39 (500 mg, 1.40 mmol) and dimethylformamide (2 drops) in dichloromethane (5 ml), and the reaction stirred at room temperature for 3 hours. The reaction mixture was concentrated under reduced pressure and azeotroped with toluene to afford the title compound as a white foam, (500 mg). LRMS: m/z 373 (M–Cl+OMe)$^+$.

Preparation 42

3-Benzyl-5-[5-(4-methylpiperazin-1ylsulphonyl)-2-n-propoxyphenyl]-1-n-propyl-1H-pyrazole-4-carbonitrile The title compound of preparation 40 (1.14 g, 3.32 mmol) was added to a suspension of the title compound of preparation 9 (360 mg, 1.50 mmol) in pyridine (5 ml) and the reaction stirred at 70° C. for 20 hours. The cooled reaction mixture was concentrated under reduced pressure, azeotroped with toluene, and the residual oil was partitioned between dichloromethane (10 ml) and sodium bicarbonate solution (20 ml). The phases were separated, the aqueous layer extracted with dichloromethane (2×15 ml), and the combined organic solutions, dried ($Na_2SO_4$) and evaporated under reduced pressure. The crude product was purified by column chromatography on silica gel, using an elution gradient of ethyl acetate:methanol (100:0 to 90:10) to afford the title compound as an off-white solid, (460 mg).

δ ($CDCl_3$): 0.94 (3H, t), 1.62 (3H, t), 1.90 (2H, m), 2.25 (3H, s), 2.46 (4H, m), 3.05 (4H, m), 3.98 (2H, t), 4.04 (2H, s), 4.40 (2H, q), 7.17 (1H, d), 7.20–7.38 (5H, m), 7.92 (1H, d), 8.59 (1H, s), 9.59 (1H, s). LRMS: m/z 551 (M+1)$^+$.

Preparation 43

3-Benzyl-5-{5-[4-(2-hydroxyethyl)piperazin-1ylsulphonyl]-(2-n-propoxy)phenyl}-1-n-propyl-1H-pyrazole-4-carboxamide A mixture of the title compounds of preparations 17 (361 mg, 1.40 mmol) and 41 (527 mg, 1.40 mmol) in pyridine (5 ml) was heated at 70° C. for 20 hours. The cooled reaction mixture was concentrated under reduced pressure, azeotroped with toluene and the residual oil partitioned between dichloromethane (10 ml) and sodium bicarbonate solution (20 ml). The phases were separated, the aqueous layer extracted with dichloromethane (2×20 ml), the combined organic solutions dried ($Na_2SO_4$) and evaporated under reduced pressure. The crude product was triturated with ether to afford the title compound as a light brown solid, (477 mg). LRMS: m/z 599 (M+1)$^+$.

Preparation 44

5-[2-Ethoxy-5-(4-methylpiperazin-1ylsulphonyl) phenyl]-1-ethyl-3-phenyl-1H-pyrazole-4-carboxamide The title compound of preparation 24 (230 mg, 1.0 mmol) was added to the title compound of preparation 40 (383 mg, 1.0 mmol) in pyridine (6 ml), and the reaction stirred at 60° C. for 18 hours. The cooled reaction mixture was concentrated under reduced pressure and azeotroped with toluene. The residual yellow foam was purified by column chromatography on silica gel, using an elution gradient of dichloromethane:methanol (95:5 to 92:8) to afford the title compound, (180 mg).

δ ($CDCl_3$): 1.52 (3H, t), 1.64 (3H, t), 2.22 (3H, s), 2.43 (4H, m), 3.02 (4H, m), 4.18 (2H, q), 4.42 (2H, q), 5.17 (1H, s), 5.43 (1H, s), 7.15 (1H, d), 7.42 (3H, m), 7.60 (2H, m), 7.87 (1H, d), 8.61 (1H, s), 10.72 (1H, s).

Preparation 45

3-[(Benzyloxy)methyl]-5-[2-ethoxy-5-(4-methylpiperazin-1-ylsulphonyl)-phenyl]-1-n-propyl-1H-pyrazole-4-carboxamide Obtained as a crystalline solid (47%) from the title compounds of preparations 19 and 40, using the procedure of preparation 43.

δ ($CDCl_3$): 0.86 (3H, t), 1.57 (3H, t), 1.81 (2H, m), 2.24 (3H, s), 2.44 (4H, m), 3.05 (4H, m), 4.01 (2H, t), 4.44 (2H, q), 4.59 (2H, s), 4.70 (2H, s), 7.08 (1H, d), 7.36 (5H, m), 7.82 (1H, d), 8.63 (1H, s), 11.32 (1H, s).

Preparation 46

5-[2-Ethoxy-5-(4-methylpiperazin-1ylsulphonyl) phenyl]-3-methyl-1-n-propyl-1H-pyrazole-4-carboxamide Obtained as a brown foam, from the title compound of preparation 40 and 5-amino-3-methyl-1-n-propyl-3-pyrazole carboxamide (WO 9307149 A1), using the procedure described in preparation 44.

δ ($CDCl_3$): 0.93 (3H, t), 1.62 (2H, m), 1.90 (2H, m), 2.26 (3H, s), 2.45 (4H, m), 3.07 (4H, m), 4.00 (2H, t), 4.41 (2H, q), 7.15 (1H, d), 7.90 (1H, d), 8.61 (1H, s), 10.44 (1H, s). LRMS: m/z 493 (M+1)$^+$.

Preparation 47

Pyridine-2-amino-5-sulphonic Acid

2-Aminopyridine (80 g, 0.85 mol) was added portionwise over 30 minutes to oleum (320 g) and the resulting solution heated at 140° C. for 4 hours. On cooling, the reaction was poured onto ice (200 g) and the mixture stirred in an ice/salt bath for a further 2 hours. The resulting suspension was filtered, the solid washed with ice water (200 ml) and cold IMS (200 ml) and dried under suction to afford the title compound as a solid, (111.3 g).

LRMS: m/z 175 (M+1)$^+$.

Preparation 48

Pyridine-2-amino-3-bromo-5-sulphonic Acid

Bromine (99 g, 0.62 mol) was added dropwise over an hour, to a hot solution of the title compound of preparation 47 (108 g, 0.62 mol) in water (600 ml) so as to maintain a steady reflux. Once the addition was complete the reaction was cooled and the resulting mixture filtered. The solid was washed with water and dried under suction to afford the title compound, (53.4 g).

δ (DMSOd$_6$): 8.08 (1H, s), 8.14 (1H, s). LRMS: m/z 253 (M)$^+$.

Preparation 49

Pyridine-3-bromo-2-chloro-5-sulphonyl Chloride

A solution of sodium nitrite (7.6 g, 110 mmol) in water (30 ml) was added dropwise to an ice-cooled solution of the title compound of preparation 48 (25.3 g, 100 mmol) in aqueous hydrochloric acid (115 ml, 20%), so as to maintain the temperature below 6° C. The reaction was stirred for 30 minutes at 0° C. and a further hour at room temperature. The reaction mixture was evaporated under reduced pressure and the residue dried under vacuum at 70° C. for 72 hours. A mixture of this solid, phosphorus pentachloride (30 g, 144 mmol) and phosphorus oxychloride (1 ml) was heated at 125° C. for 3 hours, and then cooled. The reaction mixture was poured onto ice (10 g) and the resulting solid filtered, and washed with water. The product was dissolved in dichloromethane, dried (MgSO$_4$), filtered and evaporated under reduced pressure to afford the title compound as a yellow solid, (26.6 g).

δ (CDCl$_3$): 8.46 (1H, s), 8.92 (1H, s).

Preparation 50

Pyridine-3-bromo-5-(4-ethylpiperazin-1-ylsulphonyl)-2-chloride

A solution of 1-ethyl piperazine (11.3 ml, 89 mmol) and triethylamine (12.5 ml, 89 mmol) in dichloromethane (150 ml) was added dropwise to an ice-cooled solution of the title compound of preparation 49 (23 g, 79 mmol) in dichloromethane (150 ml) and the reaction stirred at 0° C. for an hour. The reaction mixture was concentrated under reduced pressure and the residual brown oil was purified by column chromatography on silica gel, using an elution gradient of dichloromethane:methanol (99:1 to 97:3) to afford the title compound as an orange solid, (14.5 g).

δ (CDCl$_3$): 1.05 (3H, t), 2.42 (2H, q), 2.55 (4H, m), 3.12 (4H, m), 8.24 (1H, s), 8.67 (1H, s).

Preparation 51

3-Bromo-2-ethoxy-5-(4-ethylpiperazin-1-ylsulphonyl)pyridine

A mixture of the title compound of preparation 50 (6.60 g, 17.9 mmol) and sodium ethoxide (6.09 g, 89.55 mmol) in ethanol (100 ml) was heated under reflux for 18 hours, then cooled. The reaction mixture was concentrated under reduced pressure, the residue partitioned between water (100 ml) and ethyl acetate (100 ml), and the layers separated. The aqueous phase was extracted with ethyl acetate (2×100 ml), the combined organic solutions dried (MgSO$_4$) and evaporated under reduced pressure to afford the title compound as a brown solid, (6.41 g).

Found : C, 41.27; H, 5.33; N, 11.11. C$_{13}$H$_{20}$BrN$_3$O$_3$S requires C, 41.35; H, 5.28; N, 10.99%.

δ (CDCl$_3$): 1.06 (3H, t), 1.48 (2H, m), 2.42 (2H, q), 2.56 (4H, m), 3.09 (4H, m), 4.54 (2H, q), 8.10 (1H, s), 8.46 (1H, s). LRMS: m/z 380 (M+2)$^+$.

Preparation 52

Pyridine-2-ethoxy-5-(4-ethylpiperazin-1-ylsulphonyl)-3-carboxylic Acid Ethyl Ester A mixture of the title compound of preparation 51 (6.40 g, 16.92 mmol), triethylamine (12 ml),and palladium (0) tris(triphenylphosphine) in ethanol (60 ml) was heated at 100° C. and 200 psi, under a carbon monoxide atmosphere, for 18 hours, then cooled. The reaction mixture was evaporated under reduced pressure and the residue purified by column chromatography on silica gel, using an elution gradient of dichloromethane:methanol (100:0 to 97:3) to afford the title compound as an orange oil, (6.2 g).

δ (CDCl$_3$): 1.02 (3H, t), 1.39 (3H, t), 1.45 (3H, t), 2.40 (2H, q), 2.54 (4H, m), 3.08 (4H, m), 4.38 (2H, q), 4.55 (2H, q), 8.37 (1H, s), 8.62 (1H, s). LRMS: m/z 372 (M+1)$^+$.

Preparation 53

Pyridine-2-ethoxy-5-(4-ethylpiperazin-1-ylsulphonyl)-3-carboxylic Acid

A mixture of the title compound of preparation 52 (4.96 g, 13.35 mmol) and aqueous sodium hydroxide solution (25 ml, 2N) in ethanol (25 ml) was stirred at room temperature for 2 hours. The reaction mixture was concentrated under reduced pressure to half it's volume, washed with ether and acidified to pH 5 using 4N hydrochloric acid. The aqueous solution was extracted with dichloromethane (3×30 ml), the combined organic extracts dried (MgSO$_4$) and evaporated under reduced pressure to afford the title compound as a tan coloured solid, (4.02 g).

δ (DMSOd$_6$): 1.18 (3H, t), 1.37 (3H, t), 3.08 (2H, q), 3.17–3.35 (8H, m), 4.52 (2H, q), 8.30 (1H, s), 8.70 (1H, s).

Preparation 54

Pyridine-2-ethoxy-5-(4-ethylpiperazin-1-ylsulphonyl)-3-carboxylic Acid Chloride Hydrochloride Oxalyl chloride (0.77 ml, 8.85 mmol) was added dropwise to an ice-cooled solution of the title compound of preparation 53 (1.52 g, 4.42 mmol) and dimethylformamide (2 drops) in dichloromethane (30 ml) and the reaction stirred for 18 hours at room temperature. The mixture was concentrated under reduced pressure and the residue triturated with ethyl acetate. The resulting solid was filtered, washed with ether and dried under suction to afford the title compound (1.68 g).

Found: C, 41.51; H, 5.27; N, 10.32. C$_{14}$H$_{21}$Cl$_2$N$_3$O$_4$S;0.10CH$_2$Cl$_2$ requires C, 41.73; H, 5.02; N, 10.36%. δ (CDCl$_3$): 1.46 (6H, m), 2.95 (2H, q), 3.11 (2H, m), 3.48 (2H, m), 3.55 (2H, m), 3.92 (2H, m), 4.60 (2H, q), 8.58 (1H, s), 8.66 (1H, s), 13.16 (1H, s).

Preparation 55

5-[2-Ethoxy-5-(4-ethylpiperazin-1-ylsulphonyl) pyridin-3-yl]-1-ethyl-3-(pyrazin-2-yl)-1,5-dihydro-4H-pyrazolo[3,4-d]pyrimidin-4-one The title compound of preparation 22 (174 mg, 0.75 mmol) was added to a suspension of the title compound of preparation 54 (300 mg, 0.75 mmol) in pyridine (6 ml), and the reaction stirred at 60° C. for 18 hours. The cooled reaction mixture was concentrated under reduced pressure and azeotroped with toluene. The residue was purified by column chromatography on silica gel, using an elution gradient of methanol:ethyl acetate:dichloromethane (5:95:0 to 10:90:0 to 10:0:90) to afford the title compound, (170 mg).

δ (CDCl$_3$): 1.04 (3H, t), 1.60 (6H, m), 2.41 (2H, q), 2.57 (4H, m), 3.14 (4H, m), 4.24 (2H, q), 4.80 (2H, q), 5.60 (1H, s), 8.45 (1H, s), 8.60 (1H, s), 8.72 (1H, s), 8.82 (1H, s), 9.57 (1H, s), 10.57 (1H, s), 11.48 (1H, s). LRMS: m/z 558 (M+1)$^+$.

Preparation 56

5-[2-Ethoxy-5-(4-ethylpiperazin-1-ylsulphonyl) pyridin-3-yl]-1-n-propyl-3-(pyrazin-2-yl)-1,5-dihydro-4H-pyrazolo[3,4-d]pyrimidin-4-one Obtained (34%) from the title compounds of preparations 23 and 54, using the procedure described in preparation 55.

δ (CDCl$_3$): 1.00 (6H, m), 1.60 (3H, t), 2.02 (2H, m), 2.41 (2H, q), 2.55 (4H, m), 3.10 (4H, m), 4.18 (2H, t), 4.80 (2H, q), 5.60 (1H, s), 8.46 (1H, s), 8.60 (1H, s), 8.75 (1H, s), 8.83 (1H, s), 9.55 (1H, s), 10.56 (1H, s), 11.45 (1H, s). LRMS: m/z 572 (M+1)$^+$.

Preparation 57

5-[2-Ethoxy-5-(4-ethylpiperazin-1-ylsulphonyl) pyridin-3-yl]-1-ethyl-3-phenyl-1,5-dihydro-4H-pyrazolo[3,4-d]pyrimidin-4-one The title compound of preparation 24 (200 mg, 0.9 mmol) was added to a suspension of the title compound of preparation 54 (346 mg, 0.9 mmol) in pyridine (6 ml) and the reaction stirred at 60° C. for 72 hours. The cooled reaction mixture was concentrated under reduced pressure, azeotroped with toluene, and the residue partitioned between ethyl acetate (30 ml) and water (15 ml). The phases were separated, the organic layer dried (Na$_2$SO$_4$) and evaporated under reduced pressure. The residue was purified by column chromatography on silica gel, using an elution gradient of ethyl acetate:methanol (98:2 to 90:10) to afford the title compound, (70 mg).

δ (CDCl$_3$): 1.01 (3H, t), 1.56 (6H, m), 2.40 (2H, m), 2.55 (4H, m), 3.13 (4H, m), 4.48 (2H, q), 4.75 (2H, q), 7.38 (1H, m), 7.43 (2H, m), 8.39 (2H, d), 8.66 (1H, s), 9.07 (1H, s), 10.78 (1H, s). LRMS m/z: 556 (M+1)$^+$.

Preparation 58

3-[(Benzyloxy)methyl]-5-[2-ethoxy-5-(4-ethylpiperazin-1-ylsulphonyl)pyridin-3-yl]-1-ethyl-1,5-dihydro-4H-pyrazolo[3,4-d]pyrimidin-4-one A solution of the title compound of preparation 54 (4.14 g, 10 mmol) in dichloromethane (50 ml) was added dropwise to an ice cold solution of the title compound of preparation 18 (2.74 g, 10 mmol) and triethylamine (2.02 g, 20 mmol) in dichloromethane (50 ml), and the reaction stirred at room temperature for 16 hours. The reaction mixture was concentrated under reduced pressure, the residue partitioned between ether (50 ml) and 1N citric acid solution (20 ml), and the phases separated. The organic layer was extracted with 1N citric acid (2×20 ml) and the aqueous solutions extracted with dichloromethane (3×60 ml). The combined dichloromethane extracts were dried (MgSO$_4$) and evaporated under reduced pressure. The residue was purified by column chromatography on silica gel, using an elution gradient of dichloromethane:methanol (100:0 to 95:5), then repeated using ethyl acetate:methanol (100:0 to 85:15), to afford the title compound as a clear gum, (944 mg).

δ (CDCl$_3$): 1.00 (3H, t), 1.46 (3H, t), 1.58 (3H, t), 2.39 (2H, q), 2.50 (4H, m), 3.04 (4H, m), 4.10 (2H, q), 4.53 (2H, s), 4.70 (2H, s), 4.78 (2H, q), 5.22 (1H, s), 7.29 (5H, m), 7.79 (1H, s), 8.65 (1H, s), 8.80 (1H, s), 11.04 (1H, s). LRMS: m/z 600 (M+1)$^+$.

Preparation 59

6-{2-Ethoxy-5-[(4-methylpiperazin-1-ylsulphonyl] phenyl}-3-(hydroxymethyl)-1-n-propyl-1,5-dihydro-4H-pyrazolo[3,4-d]pyrimidin-4-one 10% Palladium on charcoal (1.7 g) was added portionwise to an ice cold suspension of the title compound of example 9 (1.20 g, 2.07 mmol) in methanol (50 ml) and then formic acid (5 ml) added dropwise. The mixture was heated under reflux for 6 hours, under a nitrogen atmosphere, then cooled. Palladium acetate (200 mg, 0.89 mmol), triphenylphosphine (460 mg, 1.7 mmol) and formic acid (5 ml) were added and the mixture heated under reflux for a further 8 hours. The cooled reaction mixture was filtered, the filtrate concentrated under reduced pressure and the residue partitioned between dichloromethane (40 ml) and saturated sodium bicarbonate solution (15 ml). The phases were separated, the organic layer dried (Na$_2$SO$_4$), evaporated under reduced pressure and the residue triturated with ether, to afford the title compound, (240 mg). Found : C, 53.66; H, 6.16; N, 16.79. C$_{22}$H$_{30}$N$_6$O$_5$S requires C, 53.86; H, 6.17; N, 17.13%. δ (CDCl$_3$): 1.00 (3H, t), 1.65 (3H, t), 2.00 (2H, m), 2.25 (3H, s), 2.48 (4H, m), 3.10 (4H, m), 4.20 (2H, t), 4.40 (2H, q), 5.00 (2H, s), 5.50 (1H, s), 7.18 (1H, d), 7.86 (1H, d), 8.99 (1H, s), 10.82 (1H, s). LRMS: m/z491 (M+1)$^+$.

Preparation 60

6-[2-Ethoxy-5-(4-methylpiperazin-1-ylsulphonyl) phenyl]-4-oxo-1-n-propyl-1,5-dihydro-4H-pyrazolo [3,4-d]pyrimidine-3-carbaldehyde Tetrapropylammonium perruthenate (5 mg, 0.014 mmol) was added to a suspension of the title compound of preparation 59 (130 mg, 0.26 mmol), 4Å molecular sieves (150 mg) and N-methylmorpholine N-oxide (50 mg, 0.4 mmol) in dichloromethane (5 ml) and acetonitrile (2 ml), and the reaction was stirred at room temperature for 2 hours under a nitrogen atmosphere. The reaction mixture was purified directly by column chromatography on silica gel, using an elution gradient of dichloromethane:methanol (99:1 to 94:6), to afford the title compound, (70 mg).

δ (CDCl$_3$): 0.99 (3H, t), 1.66 (3H, t), 2.00 (2H, m), 2.25 (3H, s), 2.48 (4H, m), 3.10 (4H, m), 4.40 (2H, q), 4.73 (2H, t), 7.18 (1H, d), 7.88 (1H, d), 8.98 (1H, s), 10.46 (1H, s), 10.98 (1H, s). LRMS: m/z 489 (M+1)$^+$.

Preparation 61

6-[2-Ethoxy-5-(4-methylpiperazin-1-ylsulphonyl) phenyl]-4-oxo-1-n-propyl-4,5-dihydro-1H-pyrazolo [3,4-d]pyrimidine-3-carbaldehyde N-Ethyldiisopropylamine (410 mg, 3.16 mmol) was added to a suspension of the title compound of preparation 53 (400 mg, 1.05 mmol) and 5-amino-1-cyclopentyl-3-ethyl-4-pyrazolecarboxamide (WO 9628448) (210 mg, 0.95 mmol) and 2-chloro-1-methyl pyridinium chloride (403 mg, 1.58 mmol) in dichloromethane (5 ml), and the reaction was stirred at room temperature for 72 hours. The reaction mixture was diluted with dichloromethane (30 ml), washed consecutively with water (10 ml), saturated sodium bicarbonate solution (10 ml), and brine (10 ml), dried ($MgSO_4$) and evaporated under reduced pressure. The residual oil was purified by column chromatography on silica gel, using an elution gradient of dichloromethane:methanol:0.88 ammonia (90:10:0 to 90:10:1) and repeated using dichloromethane:methanol:0.88 ammonia (100:0:1 to 94:4: 1) to afford the title compound, (263 mg).

δ ($CDCl_3$): 1.04 (3H, t), 1.33 (3H, t), 1.58 (3H, t), 1.65 (2H, m), 1.94 (2H, m), 2.10 (4H, m), 2.41 (2H, q), 2.54 (4H, m), 2.81 (2H, q), 3.10 (4H, m), 4.52 (1H, m), 4.79 (2H, q), 5.58 (2H, s), 8.69 (1H, s), 8.82 (1H, s), 10.45 (1H, s). LRMS: m/z 548 $(M+1)^+$.

Synthesis of the Compounds of Formulae IA and IB

Example 1

6-[5-(4-Ethylpiperazin-1-ylsulphonyl)-2-n-propoxyphenyl]-1-n-propyl-3-(pyridin-2-yl)methyl-1,5-dihydro-4H-pyrazolo[3,4-d]pyrimidin-4-one A mixture of the title compound of preparation 37 (32 mg, 0.08 mmol), chlorosulphonic acid (140 mg, 1.2 mmol) and thionyl chloride (48 mg, 0.40 mmol) in dichloromethane (0.5 ml) was stirred at room temperature for 18 hours. Ice (2 g) was added, followed by a solution of N-ethylpiperazine (570 mg, 5 mmol) in dichloromethane (20 ml) and the reaction stirred for a further hour. The mixture was poured into water (20 ml), the layers separated and the aqueous phase extracted with dichloromethane (3×20 ml). The combined organic solutions were dried ($MgSO_4$) and evaporated under reduced pressure. The residue was purified by column chromatography on silica gel, using an elution gradient of dichloromethane:methanol (100:0 to 95:5) to afford the title compound, (42 mg).

δ ($CDCl_3$): 0.84 (3H, t), 0.98 (3H, t), 1.16 (3H, t), 1.83 (2H, m), 2.00 (2H, m), 2.36 (2H, q), 2.48 (4H, m), 3.02 (4H, m), 4.20 (2H, t), 4.26 (2H, t), 4.63 (2H, s), 7.12 (2H, m), 7.38 (1H, d), 7.57 (1H, m), 7.80 (1H, d), 8.45 (1H, d), 8.93 (1H, s), 10.60 (1H, s). LRMS: m/z 580 $(M+1)^+$.

Example 2

6-[5-(4-Methylpiperazin-1-ylsulphonyl)-2-n-propoxyphenyl]-1-n-propyl-3-(pyrimidin-2-yl) methyl-1,5-dihydro-4H-pyrazolo[3,4-d]pyrimidin-4-one Obtained as a white solid (38%) from the title compound of preparation 38 and N-methylpiperazine, using a similar procedure to that described in example 1, except purification was achieved by ether trituration.

Found: C, 54.14; H, 5.83; N, 18.61. $C_{27}H_{34}N_8O_4S;0.5CH_2Cl_2$ requires C, 54.22; H, 5.79; N, 18.39%. δ ($CDCl_3$): 0.84 (3H, t), 1.14 (3H, t), 1.86 (2H, m), 1.99 (2H, m), 2.22 (3H, s), 2.45 (4H, m), 3.04 (4H, m), 4.15 (2H, t), 4.20 (2H, t), 4.84 (2H, s), 7.12 (2H, m), 7.80 (1H, d), 8.62 (2H, d), 8.96 (1H, s), 10.55 (1H, s). LRMS: m/z 567 $(M+1)^+$.

Example 3

6-[5-(4-Ethylpiperazin-1-ylsulphonyl)-2-n-propoxyphenyl]-1-n-propyl-3-(pyrimidin-2-yl) methyl-1,5-dihydro-4H-pyrazolo[3,4-d]pyrimidin-4-one Obtained as a pale pink solid (45%) from the title compound of preparation 38 and N-ethylpiperazine, using a similar procedure to that described in example 1, except purification was achieved by diethyl ether trituration.

Found : C, 55.26; H, 6.37; N, 18.46. $C_{28}H_{36}N_8O_4S;1.5H_2O$ requires C, 55.34; H, 6.47; N, 18.44%. δ ($CDCl_3$): 0.84 (3H, t), 0.99 (3H, t), 1.14 (3H, t), 1.86 (2H, m), 1.98 (2H, m), 2.38 (2H, q), 2.48 (4H, m), 3.03 (4H, m), 4.14 (2H, t), 4.20 (2H, t), 4.84 (2H, s), 7.12 (2H, m), 7.81 (1H, d), 8.63 (2H, d), 8.94 (1H, s), 10.54 (1H, s). LRMS: m/z 581 $(M+1)^+$.

Example 4

3-Benzyl-6-[2-ethoxy-5-(4-methylpiperazin-1-ylsulphonyl)phenyl]-1-n-propyl-1,5-dihydro-4H-pyrazolo[3,4-d]pyrimidin-4-one Powdered potassium hydroxide (78 mg, 1.38 mmol) was added to a suspension of the title compound of preparation 42 (254 mg, 0.46 mmol) in 3-methyl-3-pentanol (5 ml), and the reaction heated at 110° C. for 18 hours. The cooled reaction mixture was partitioned between ethyl acetate (10 ml) and water (10 ml), the phases separated, and the aqueous layer extracted with further ethyl acetate (2×10 ml). The combined organic solutions were dried ($Na_2SO_4$), and evaporated under reduced pressure. The residual oil was purified by column chromatography on silica gel, using an elution gradient of dichloromethane:methanol:0.88 ammonia (100:0:0 to 85:15:1) to afford the title compound as a white foam, (23 mg).

Found: C, 60.44; H, 6.15; N, 14.92. $C_{28}H_{34}N_6O_4S$ requires C, 61.05; H, 6.18; N, 15.26%. δ ($CDCl_3$): 0.94 (3H, t), 1.65 (3H, t), 1.97 (2H, m), 2.26 (3H, s), 2.48 (4H, m), 3.08 (4H, m), 4.35 (6H, m), 7.18 (2H, m), 7.26 (2H, m), 7.47 (2H, m), 7.86 (1H, d), 8.82 (1H, s), 10.70 (1H, s). LRMS: m/z 551 $(M+1)^+$.

Example 5

3-Benzyl-6-{2-ethoxy-5-[4-(2-hydroxyethyl) piperazin-1-ylsulphonyl]phenyl}-1-n-propyl-1,5-dihydro-4H-pyrazolo[3,4-d]pyrimidin-4-one A mixture of the title compound of preparation 43 (477 mg, 0.80 mmol) and potassium t-butoxide (313 mg, 2.79 mmol) in isopropanol (25 ml), was heated under reflux for 18 hours, then cooled. Water (50 ml) was added, the mixture neutralised with 2N hydrochloric acid and concentrated under reduced pressure. This solution was partitioned between ethyl acetate (50 ml) and sodium bicarbonate solution (25 ml), the layers separated and the aqueous phase extracted with ethyl acetate (2×25 ml). The combined organic solutions were dried ($Na_2SO_4$) and evaporated under reduced pressure. The residual brown oil was purified by column chromatography on silica gel, using an elution gradient of dichloromethane:methanol (100:0 to 95:5), and triturated with ether to afford the title compound, (112 mg).

Found: C, 59.63; H, 6.22; N, 14.34. $C_{29}H_{36}N_6O_5S$ requires C, 59.98; H, 6.20; N, 14.49%. δ ($CDCl_3$): 0.95 (3H, t), 1.63 (3H, t), 1.96 (2H, m), 2.26 (1H, s), 2.55 (2H, t), 2.60 (4H, m), 3.09 (4H, m), 3.58 (2H, m), 4.35 (6H, m), 7.18 (2H, d), 7.26 (2H, m), 7.46 (2H, m), 7.87 (1H, d), 8.83 (1H, s), 10.70 (1H, s). LRMS: m/z 581 (M+1)$^+$.

Example 6

6-[2-Ethoxy-5-(4-methylpiperazin-1-ylsulphonyl) phenyl]-1-ethyl-3-phenyl-1,5-dihydro-4H-pyrazolo [3,4-d]pyrimidin-4-one

A mixture of the title compound of preparation 44 (180 mg, 0.34 mmol) and potassium t-butoxide (116 mg, 1.0 mmol) in ethanol (10 ml) was heated under reflux for 4 hours. The cooled reaction mixture was evaporated under reduced pressure and the residue purified by column chromatography on silica gel, using an elution gradient of dichloromethane:methanol (100:0 to 95:5) to afford the title compound, (110 mg).

Found: C, 58.74; H, 5.88; N, 15.66. $C_{26}H_{30}N_6O_4S$ requires C, 58.74; H, 5.88; N, 15.81%. δ ($CDCl_3$) 1.58 (3H, t), 1.69 (3H, t), 2.27 (3H, s), 2.52 (4H, m), 3.14 (4H, m), 4.40 (2H, q), 4.51 (4H, q), 7.19 (1H, d), 7.39 (1H, m), 7.45 (1H, m), 7.90 (1H, d), 8.42 (1H, d), 8.90 (1H, s), 10.88 (1H, s). LRMS: m/z 523 (M+1)$^+$.

Example 7

1-Ethyl-6-[5-(4-methylpiperazin-1-ylsulphonyl)-2-n-propoxyphenyl]-3-phenyl-1,5-dihydro-4H-pyrazolo [3,4-d]pyrimidin-4-one

A suspension of sodium (25 mg, 1.1 mmol) in n-propanol (1 ml) was added to the title compound of example 6 (80 mg, 0.15 mmol) in n-propanol (1 ml), and the reaction mixture heated under reflux for 72 hours. Further sodium (100 mg, 4.34 mmol) and n-propanol (5 ml) were added portionwise over a further 48 hours, then the mixture cooled and evaporated under reduced pressure. The residue was purified by preparative thin layer chromatography on silica gel, using dichloromethane:methanol:0.88 ammonia (95:5:0.5) as eluant, to afford the title compound, (8 mg).

δ ($CDCl_3$): 1.19 (3H, t), 1.58 (3H, t), 2.02 (2H, m), 2.28 (3H, s), 2.52 (4H, m), 3.13 (4H, m), 4.24 (2H, t), 4.48 (2H, q), 7.18 (1H, d), 7.37 (1H, m), 7.43 (2H, m), 7.86 (1H, d), 8.40 (2H, d), 8.86 (1H, s), 10.90 (1H, s). LRMS: m/z 536 (M+1)$^+$.

Example 8

3-(Benzyloxy)methyl-6-[2-isopropoxy-5-(4-methylpiperazin-1-ylsulphonyl)phenyl]-1-n-propyl-1,5-dihydro-4H-pyrazolo[3,4-d]pyrimidin-4-one and

Example 9

3-(Benzyloxy)methyl-6-[2-ethoxy-5-(4-methylpiperazin-1-ylsulphonyl)phenyl]-1-n-propyl-1,5-dihydro-4H-pyrazolo[3,4-d]pyrimidin-4-one

A mixture of the title compound of preparation 45 (1.80 g, 3.1 mmol) and potassium t-butoxide (1.4 g, 12.4 mmol) in isopropanol (40 ml) was heated under reflux for 10 hours and stirred for a further 16 hours at room temperature. Water (5 ml) was added, the mixture acidified to pH 6 with 2N hydrochloric acid, and concentrated under reduced pressure to remove the isopropanol and the resulting precipitate filtered and dried. This solid was purified by column chromatography on silica gel, using an elution gradient of dichloromethane:methanol (99:1 to 92:8) and repeated using an elution gradient of dichloromethane:isopropanol:0.88 ammonia (98:2:0.1 to 90:10:0.5) to afford, after trituration with ethyl acetate, the title compound of example 8, (15 mg).

δ ($CDCl_3$): 0.96 (3H, t), 1.59 (6H, d), 2.03 (2H, m), 2.48 (3H, s), 2.50 (4H, m), 3.10 (4H, m), 4.30 (2H, t), 4.62 (2H, s), 4.92 (1H, m), 5.05 (2H, s), 7.17 (1H, d), 7.34 (5H, m), 7.84 (1H, d), 9.00 (1H, s), 10.76 (1H, s). LRMS: m/z 595 (M+1)$^+$.

and the title compound of example 9, (320 mg).

Found: C, 59.78; H, 6.21; N, 14.37. $C_{29}H_{36}N_6O_5S$ requires C, 59.98; H, 6.25; N, 14.47%. δ ($CDCl_3$): 0.97 (3H, t), 1.64 (3H, t), 2.02 (2H, m), 2.26 (3H, s), 2.48 (4H, m), 3.10 (4H, m), 4.30 (2H, t), 4.39 (2H, q), 4.61 (2H, s), 5.05 (2H, s), 7.17 (1H, d), 7.34 (5H, m), 7.82 (1H, d), 8.98 (1H, s), 10.64 (1H, s). LRMS:m/z 581 (M+1)$^+$.

Example 10

6-[2-Ethoxy-5-(4-methylpiperazin-1-ylsulphonyl) phenyl]-3-methyl-1-n-propyl-1,5-dihydro-4H-pyrazolo[3,4-d]pyrimidin-4-one

Obtained as an off-white solid (43%) from the title compound of preparation 46, using a similar procedure to that described in example 5, except the title compound was isolated by trituration with diethyl ether.

δ ($CDCl_3$): 0.95 (3H, t), 1.64 (3H, t), 1.97 (2H, m), 2.27 (3H, s), 2.50 (4H, m), 2.62 (3H, s), 3.12 (4H, m), 4.30 (2H, t), 4.40 (2H, q), 7.19 (1H, d), 7.89 (1H, d), 8.82 (1H, s), 10.68 (1H, s). LRMS: m/z 475 (M+1)$^+$.

Example 11

6-[2-Ethoxy-5-(4-methylpiperazin-1-ylsulphonyl) phenyl]-3-isopropoxy-1-n-propyl-1,5-dihydro-4H-pyrazolo[3,4-d]pyrimidin-4-one

A solution of the title compound of preparation 40 (730 mg, 1.4 mmol) in dichloromethane (3 ml) was added dropwise to solution of the title compound of preparation 20 (243 mg, 1.2 mmol) in pyridine (10 ml), and the reaction stirred at room temperature for 5 days. The reaction mixture was concentrated under reduced pressure and azeotroped with toluene. The residual orange solid was purified by column chromatography on silica gel, using an elution gradient of dichloromethane:methanol (99:1 to 90:10), the product suspended in dichloromethane and the suspension filtered. The filtrate was concentrated under reduced pressure and the residue partitioned between ethyl acetate (25 ml) and water (10 ml), the phases separated, the organic layer washed with brine (10 ml), dried ($MgSO_4$) and evaporated under reduced pressure, to afford the title compound as a cream foam, (48 mg).

δ ($CDCl_3$): 0.90 (3H, t), 1.38 (6H, d), 1.62 (3H, t), 1.89 (2H, m), 2.26 (3H, s), 2.48 (4H, m), 3.05 (4H, m), 3.26 (1H, m), 4.00 (2H, t), 4.42 (2H, q), 7.18 (1H, d), 7.92 (1H, d), 8.62 (1H, s), 10.22 (1H, s). LRMS m/z 521 (M+18)$^+$.

Example 12

3-(Cyclopropyl)methyl-6-[2-ethoxy-5-(4-methylpiperazin-1-ylsulphonyl)phenyl]-1-n-propyl-1,5-dihydro-4H-pyrazolo[3,4-d]pyrimidin-4-one

The title compound of preparation 40 (490 mg, 1.4 mmol) was added to a solution of the title compound of preparation 21 (250 mg, 1.13 mmol) in pyridine (6 ml) and the reaction stirred at room temperature for 18 hours. The reaction mixture was concentrated under reduced pressure, azeotroped with toluene and the residue partitioned between dichloromethane (40 ml) and sodium bicarbonate solution (20 ml). The phases were separated, the organic layer washed with brine (20 ml), dried (MgSO$_4$) and evaporated under reduced pressure to give a yellow oil. A mixture of this intermediate carboxamide, and potassium t-butoxide (380 mg, 3.38 mmol) in isopropanol (5 ml) was heated under reflux for 18 hours, then cooled. The reaction mixture was concentrated under reduced pressure, the residue partitioned between ethyl acetate (15 ml) and water (15 ml) and the layers separated. The aqueous layer was neutralised with 2N hydrochloric acid, extracted with ethyl acetate (3×15 ml), and these combined organic extracts washed with brine (20 ml), dried (MgSO$_4$) and evaporated under reduced pressure. The crude product was purified by column chromatography on silica gel twice, using an elution gradient of dichloromethane:isopropanol (99:1 to 90:10) to afford the title compound, (60 mg).

δ (CDCl$_3$): 0.34 (2H, m), 0.46 (2H, m), 0.95 (3H, t), 1.30 (1H, m), 1.65 (3H, t), 1.98 (2H, m), 2.28 (3H, s), 2.51 (4H, m), 2.90 (2H, m), 3.10 (4H, m), 4.38 (4H, m), 7.18 (1H, d), 7.86 (1H, d), 8.83 (1H, s), 10.70 (1H, s). LRMS: m/z 515 (M+1)$^+$.

Example 13

6-[2-Ethoxy-5-(4-methylpiperazin-1-ylsulphonyl)phenyl]-3-(morpholinomethyl)-1-n-propyl-1,5-dihydro-4H-pyrazolo[3,4-d]pyrimidin-4-one A mixture of the title compound of preparation 60 (70 mg, 0.14 mmol), morpholine (15 ml, 0.17 mmol), sodium triacetoxyborohydride (43 mg, 0.20 mmol) and acetic acid (10 ml, 0.17 mmol) in dichloromethane (2 ml) was stirred at room temperature for 18 hours. The reaction mixture was partitioned between dichloromethane (10 ml) and dilute sodium bicarbonate solution (10 ml), the phases separated and the aqueous layer extracted with dichloromethane (2×10 ml). The combined organic solutions were dried (Na$_2$SO$_4$) and evaporated under reduced pressure. The residue was purified by column chromatography on silica gel, using an elution gradient of dichloromethane:methanol (99:1 to 94:6) and recrystallised from ethyl acetate, to afford the title compound, (30 mg).

δ (CDCl$_3$): 1.00 (3H, t), 1.63 (3H, t), 2.05 (2H, m), 2.26 (3H, s), 2.48 (4H, m), 2.58 (4H, t), 3.09 (4H, m), 3.67 (4H, t), 4.00 (2H, s), 4.36 (4H, m), 7.16 (1H, d), 7.84 (1H, d), 9.00 (1H, s), 10.62 (1H, s). LRMS: m/z 560 (M+1)$^+$.

Example 14

3-Methyl-6-[5-(4-methylpiperazin-1-ylsulphonyl)-2-n-propoxyphenyl]-1-(pyridin-2-yl)methyl-1,5-dihydro-4H-pyrazolo[3,4-d]pyrimidin-4-one A mixture of the title compound of preparation 28 (85 mg, 0.23 mmol) in chlorosulphonic acid (264 mg, 2.3 mmol) and thionyl chloride (81 mg, 0.68 mmol) was stirred at room temperature for 18 hours. The mixture was cooled in an ice-bath, ice (1 g) added, followed by ethanol (5 ml) and N-methylpiperazine (340 mg, 3.4 mmol), and the reaction stirred for 15 minutes at room temperature. The mixture was evaporated under reduced pressure and the residue purified by column chromatography on silica gel, using an elution gradient of dichloromethane:methanol (98:2 to 92:8) to afford the title compound, (89 mg).

Found: C, 57.13; H, 5.81; N, 17.79. C$_{26}$H$_{31}$N$_7$O$_4$S;0.5H$_2$O requires C, 57.13; H, 5.90; N, 17.94%. δ (CDCl$_3$): 1.17 (3H, t), 2.02 (2H, m), 2.21 (3H, s), 2.42 (4H, m), 2.60 (3H, s), 3.02 (4H, m), 4.23 (2H, t), 5.62 (2H, s), 7.03 (1H, d), 7.16 (2H, m), 7.60 (1H, m), 7.82 (1H, d), 8.57 (1H, d), 8.75 (1H, s), 10.73 (1H, s). LRMS: m/z 538 (M+1)$^+$.

Example 15

1-Cyclopentyl-3-ethyl-6-[5-(4-ethylpiperazin-1-ylsulphonyl)-2-n-propoxyphenyl]-1,5-dihydro-4H-pyrazolo[3,4-d]pyrimidin-4-one 1-Cyclopentyl-3-ethyl-6-(2-n-propoxyphenyl)-1,5-dihydro-4H-pyrazolo[3,4-d]pyrimidin-4-one (WO 96/28448) (500 mg, 1.36 mmol) was added portionwise to chlorosulphonic acid (1.6 g, 13.6 mmol) and the reaction stirred at room temperature for 18 hours. The reaction was poured into a mixture of ice water (30 ml) and dichloromethane (30 ml) with stirring, the layers separated and the aqueous extracted with dichloromethane (2×30 ml). The combined organic solutions were washed with brine (30 ml), dried (Na$_2$SO$_4$) and evaporated under reduced pressure, to give a foam. N-Ethylpiperazine (108 mg, 0.95 mmol) was added dropwise to an ice-cold solution of this intermediate sulphonyl chloride in dichloromethane (3 ml) and the reaction stirred at room temperature for 2 hours. The mixture was diluted with dichloromethane (10 ml), washed consecutively with water (5 ml), saturated sodium bicarbonate solution (5 ml) and brine (5 ml), dried (Na$_2$SO$_4$) and evaporated under reduced pressure. The residue was purified by column chromatography on silica gel, using an elution gradient of dichloromethane:methanol (100:0 to 96:4) to afford the title compound, (81 mg).

Found: C, 59.30; H, 7.06; N, 15.48. C$_{27}$H$_{38}$N$_6$O$_4$S requires C, 59.75; H, 7.06; N, 15.48%. δ (CDCl$_3$): 1.02 (3H, t), 1.19 (3H, t), 1.38 (3H,t ) 1.75 (2H, m), 2.02 (4H, m), 2.16 (4H, m), 2.40 (2H, q), 2.54 (4H, m), 2.98 (2H, q), 3.10 (4H, m), 5.25 (2H, t), 5.18 (1H, m), 7.18 (1H, d), 7.86 (1H, d), 8.84 (1H, s), 10.70 (1H, s). LRMS: m/z 543 (M+1)$^+$.

Example 16

3-Methyl-6-[5-(4-methylpiperazin-1-ylsulphonyl)phenyl]-2-(pyridin-2-yl)methyl-2,5-dihydro-4H-pyrazolo[3,4-d]pyrimidin-4-one Obtained (19%) from the title compound of preparation 29, using the procedure of example 14.

δ (CDCl$_3$): 1.14 (3H, t), 2.00 (2H, m), 2.22 (3H, s), 2.44 (4H, m), 2.72 (3H, s), 3.02 (4H, m), 4.22 (2H, t), 5.54 (2H, s), 7.11 (1H, d), 7.20 (2H, m), 7.62 (1H, m), 7.82 (1H, d), 8.55 (1H, d), 8.94 (1H, s), 10.52 (1H, s). LRMS: m/z 538 (M+1)$^+$.

Example 17

3-Methyl-6-[5-(4-methylpiperazin-1-ylsulphonyl)-2-n-propoxyphenyl]-2-(pyrimidin-2-yl)-2,5-dihydro-4H-pyrazolo[3,4-d]pyrimidin-4-one Obtained (59%) from the title compound of preparation 30, using the procedure of example 14.

Found: C, 53.65; H, 5.48; N, 20.63. C$_{24}$H$_{28}$N$_8$O$_4$S;0.8H$_2$O requires C, 53.48; H, 5.54; N, 20.79%. δ (CDCl$_3$): 1.22 (3H, t), 2.06 (2H, m), 2.27 (3H, s), 2.50 (4H, m), 3.10 (4H, m), 3.19 (3H, s), 4.30 (2H, t), 7.18 (1H, d), 7.38 (1H, m), 7.88 (1H, d), 8.90 (2H, d), 9.05 (1H, s). LRMS: m/z 525 (M+1)$^+$.

Example 18

6-[2-Ethoxy-5-(4-ethylpiperazin-1-ylsulphonyl) pyridin-3-yl]-1-ethyl-3-(pyrazin-2-yl)-1,5-dihydro-4H-pyrazolo[3,4-d]pyrimidin-4-one Potassium t-butoxide (103 mg, 0.9 mmol) was added to a suspension of the title compound of preparation 55 (170 mg, 0.3 mmol) in ethanol (5 ml) and the reaction stirred at 100° C. in a sealed vessel for 5 hours. The cooled reaction mixture was evaporated under reduced pressure and the residue purified by column chromatography on silica gel, using dichloromethane:methanol (85:15) as eluant, to afford the title compound as a brown solid, (130 mg).

Found: C, 51.32; H, 5.31; N, 21.90. $C_{24}H_{29}N_9O_4S;1.4H_2O$ requires C, 51.04; H, 5.67; N, 22.32%. δ (CDCl$_3$) 1.04 (3H, t), 1.62 (6H, m), 2.42 (2H, q), 2.59 (4H, m), 3.18 (4H, m), 4.61 (2H, q), 4.80 (2H, q), 8.61 (1H, s), 8.75 (2H, m), 9.13 (1H, s), 10.00 (1H, s), 10.92 (1H, s). LRMS: n/z 540 (M+1)$^+$.

Example 19

6-[2-Ethoxy-5-(4-ethylpiperazin-1-ylsulphonyl) pyridin-3-yl]-1-n-propyl-3-(pyrazin-2-yl)-1,5-dihydro-4H-pyrazolo[3,4-d]pyrimidin-4-one Obtained (45%) from the title compound of preparation 56, using a similar procedure to that described in example 18, but using ethyl acetate:methanol (90:10) as chromatographic eluant.

δ (CDCl$_3$): 1.01 (6H, m), 1.62 (3H, t), 2.08 (2H, m), 2.43 (2H, q), 2.58 (4H, m), 3.17 (4H, m), 4.55 (2H, t), 4.81 (2H, q), 8.61 (1H, s), 8.75 (2H, m), 9.14 (1H, s), 9.99 (1H, s), 10.90 (1H, s). LRMS: m/z 554 (M+1)$^+$.

Example 20

1-Ethyl-6-[5-(4-ethylpiperazin-1-ylsulphonyl)-2-(isopropoxy)pyridin-3-yl]-3-(pyrazin-2-yl)-1,5-dihydro-4H-pyrazolo[3,4d]pyrimidin-4-one A mixture of the title compound of example 18 (80 mg, 0.15 mmol) and potassium t-butoxide (50 mg, 0.44 mmol) in isopropanol (4 ml) was heated under reflux for 48 hours. The cooled reaction mixture was evaporated under reduced pressure and the residual brown solid purified by column chromatography on silica gel, using ethyl acetate:methanol (90:10) as eluant, to afford the title compound, (30 mg).

Found: C, 53.22; H, 5.77; N, 21.60. $C_{25}H_{31}N_9O_4S$; 0.5H$_2$O;0.2C$_2$H$_5$O$_2$CH$_3$ requires C, 53.40; H, 5.84; N, 21.72%. δ (CDCl$_3$): 1.04 (3H, t), 1.60 (9H, m), 2.43 (2H, q), 2.59 (4H, m), 3.18 (4H, m), 4.60 (2H, q), 5.76 (1H, m), 8.61 (1H, s), 8.74 (2H, m), 9.14 (1H, s), 9.99 (1H, s), 11.01 (1H, s). LRMS: m/z 554 (M+1)$^+$.

Example 21

6-[2-Ethoxy-5-(4-ethylpiperazin-1-ylsulphonyl) pyridin-3-yl]-1-ethyl-3-phenyl-1,5-dihydro-4H-pyrazolo[3,4-d]pyrimidin-4-one Obtained (38%) from the title compound of preparation 57, using a similar procedure to that described in example 18, but using ethyl acetate:methanol (95:5) as chromatographic eluant.

δ (CDCl$_3$): 1.01 (3H, t), 1.56 (6H, m), 2.40 (2H, q), 2.56 (4H, m), 3.13 (4H, m), 4.46 (2H, q), 4.76 (2H, q), 7.38 (1H, m), 7.43 (2H, m), 8.39 (2H, d), 8.66 (1H, s), 9.07 (1H, s), 10.78 (1H, s). LRMS: m/z 539 (M+2)$^+$.

Example 22

1-Ethyl-6-[5-(4-ethylpiperazin-1-ylsulphonyl)-2-(2-methoxyethoxy)pyridin-3-yl]-3-phenyl-1,5-dihydro-4H-pyrazolo[3,4-d]pyrimidin-4-one A mixture of potassium bis(trimethylsilyl)amide (359 mg, 1.8 mmol) in 2-methoxyethanol (20 ml) was heated at 90° C. for 30 minutes, then cooled to room temperature. The title compound of example 21 (200 mg, 0.36 mmol) was added and the reaction heated under reflux for 18 hours and allowed to cool. The mixture was concentrated under reduced pressure, the residue partitioned between ethyl acetate (20 ml) and water (20 ml) and the phases separated. The aqueous layer was extracted with ethyl acetate (2×20 ml), the combined organic solutions dried (Na$_2$SO$_4$), and evaporated under reduced pressure. The residue was purified by column chromatography on silica gel, using dichloromethane:methanol (97:3) as eluant, to afford the title compound, (105 mg).

Found: C, 56.83; H, 5.88; N, 16.99. $C_{27}H_{33}N_7O_5S$ requires C, 57.13; H, 5.86; N, 17.27%. δ (CDCl$_3$): 1.04 (3H, t), 1.59 (3H, t), 2.42 (2H, q), 2.58 (4H, m), 3.17 (4H, m), 3.59 (3H, s), 3.88 (2H, t), 4.51 (2H, q), 4.81 (2H, t), 7.39 (1H, m), 7.45 (2H, m), 8.40 (2H, m), 8.70 (1H, s), 9.04 (1H, s), 10.92 (1H, s). LRMS: m/z 568 (M+1)$^+$.

Example 23

3-(Benzyloxy)methyl-6-[2-ethoxy-5-(4-ethylpiperazin-1-ylsulphonyl)pyridin-3-yl]-1-ethyl-1,5-dihydro-4H-pyrazolo[3,4-d]pyrimidin-4-one A mixture of the title compound of preparation 58 (940 mg, 1.57 mmol) and sodium ethoxide (272 mg, 4.0 mmol) in ethanol (25 ml) was heated under reflux for 8 hours. The cooled reaction mixture was diluted with water (25 ml), and the mixture extracted with dichloromethane (3×50 ml). The combined organic extracts were dried (MgSO$_4$) and evaporated under reduced pressure, to afford the title compound, (767 mg).

δ (CDCl$_3$): 1.00 (3H, t), 1.55 (6H, m), 2.39 (2H, q), 2.52 (4H, m), 3.12 (4H, m), 4.40 (2H, q), 4.75 (4H, m), 4.85 (2H, s), 7.30 (3H, m), 7.40 (2H, m), 8.64 (1H, s), 9.04 (1H, s), 10.69 (1H, s). LRMS: m/z 582 (M+1)$^+$.

Example 24

6-[2-Ethoxy-5-(4-ethylpiperazin-1-ylsulphonyl) pyridin-3-yl]-1-ethyl-3-hydroxymethyl-1,5-dihydro-4H-pyrazolo[3,4-d]pyrimidin-4-one Formic acid (1.5 ml) was added to a mixture of the title compound of example 23 (750 mg, 1.3 mmol) and 10% palladium on charcoal (750 mg) in ethyl acetate (15 ml), and the reaction stirred under a nitrogen atmosphere at room temperature for 24 hours. The reaction mixture was filtered through Arbocel, the filter pad washed with water (30 ml) and ethyl acetate (30 ml), and the filtrate basified using 2N sodium hydroxide solution. The layers were separated, the aqueous extracted with dichloromethane (3×100 ml), and the combined organic solutions dried (MgSO$_4$) and evaporated under reduced pressure. The residue was triturated with ether, to afford the title compound as a white solid, (375 mg).

δ (CDCl$_3$): 1.02 (3H, t), 1.54 (3H, t), 1.60 (3H, t), 2.42 (2H, q), 2.57 (4H, m), 3.16 (4H, m), 4.42 (2H, q), 4.60 (1H, t), 4.79 (2H, q), 4.92 (2H, d), 8.70 (1H, s), 9.08 (1H, s), 10.88 (1H, s). LRMS: m/z 492 (M+1)$^+$.

Example 25

1-Cyclopentyl-6-[2-ethoxy-5-(4-ethylpiperazin-1-ylsulphonyl)pyridin-3-yl]-3-ethyl-1,5-dihydro-4H-pyrazolo[3,4-d]pyrimidin-4-one A mixture of the title compound of preparation 61 (253 mg, 0.46 mmol) and potassium bis(trimethylsilyl)amide (110 mg, 0.55 mmol) in ethanol (10 ml) was heated in a sealed vessel at 110° C., for 18 hours, then cooled. The reaction mixture was concentrated under reduced pressure, the residue dissolved in dichloromethane (30 ml), the solution washed with water (20 ml), and the pH of the mixture adjusted to 8 using hydrochloric acid. The layers were separated, the organic washed with brine (10 ml), dried (MgSO$_4$) and evaporated under reduced pressure. The residual oil was purified by column chromatography on silica gel, using an elution gradient of dichloromethane saturated with 0.88 ammonia:methanol (100:0 to 96.4:0.4), to afford the title compound as a white foam, (210 mg).

Found: C, 56.51; H, 6.71; N, 18.16. $C_{25}H_{35}N_7O_4S$ requires C, 56.69; H, 6.66; N, 18.51%. δ (CDCl$_3$): 1.03 (3H, t), 1.38 (3H, t), 1.59 (3H, t), 1.75 (2H, m), 2.00 (2H, m), 2.16 (4H, m), 2.42 (2H, q), 2.57 (4H, m), 2.99 (2H, q), 3.15 (4H, m), 4.77 (2H, q), 5.19 (1H, m), 8.68 (1H, s), 9.07 (1H, s), 10.62 (1H, s). LRMS: m/z 530 (M+1)$^+$.

Biological Activity

Compounds of the invention were found to have in vitro activities as inhibitors of cGMP PDE5 with IC$_{50}$ values of less than about 100 nM.

The following illustrates the in vitro activities for a range of compounds of the invention as inhibitors of cGMP PDE5.

| Example | IC$_{50}$ (nM) |
|---------|----------------|
| 1  | 9.30 |
| 4  | 5.61 |
| 14 | 4.40 |
| 18 | 8.10 |
| 19 | 7.67 |
| 21 | 4.60 |

What is claimed is:

1. A compound of formula IA, or of formula IB:

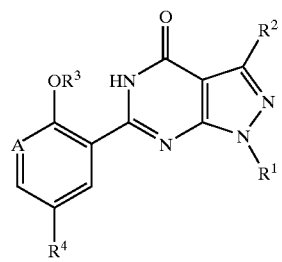

IA

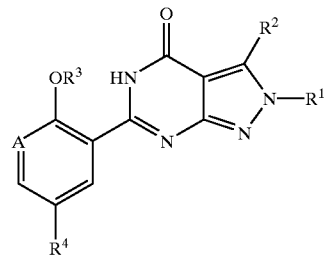

IB wherein

A represents CH or N;

R$^1$ and R$^2$ independently represent H, lower alkyl, Het, alkylHet, aryl or alkylaryl, which latter five groups are all optionally substituted by one or more substituents selected from halo, cyano, nitro, lower alkyl, OR$^5$, C(O)R$^6$, C(O)OR$^7$, C(O)NR$^8$R$^9$, NR$^{10a}$R$^{10b}$ and SO$_2$NR$^{11a}$R$^{11b}$;

R$^3$ represents H or lower alkyl, which latter group is optionally substituted by one or more substituents selected from aryl, Het, halo, cyano, nitro, OR$^5$, C(O)R$^6$, C(O)OR$^7$, C(O)NR$^8$R$^9$ and NR$^{10a}$R$^{10b}$ and SO$_2$NR$^{11a}$R$^{11b}$;

R$^4$ represents SO$_2$NR$^{12}$R$^{13}$;

R$^{12}$ and R$^{13}$, together with the nitrogen to which they are attached, form Het; Het represents an optionally-substituted four- to twelve-membered heterocyclic group, which group contains at least one nitrogen atom and, optionally, one or more further heteroatoms selected from nitrogen, sulphur and oxygen; and R$^5$, R$^6$, R$^7$, R$^8$, R$^9$, R$^{10a}$, R$^{10b}$, R$^{11a}$ and R$^{11b}$ independently represent H or lower alkyl; or a pharmaceutically, or a veterinarily acceptable salt, solvate or protected derivative thereof; provided that, when the compound is a compound of formula IA, in which R$^1$ represents C$_{1-6}$ alkyl, R$^2$ represents H, methyl or ethyl, R$^3$ represents C$_{2-4}$ alkyl and A represents CH, then R$^{12}$ and R$^{13}$, together with the nitrogen to which they are attached, do not form a pyrrolidinyl, piperidinyl, morpholinyl, 1-imidazoyl or a 4-R$^{14}$-piperazinyl (in which R$^{14}$ represents H, C$_{1-3}$ alkyl or hydroxyC$_{2-3}$alkyl) group, which pyrrolidinyl, piperidinyl, morpholinyl, 1-imidazoyl or 4-R$^{14}$-piperazinyl groups are optionally substituted by one or two C$_{1-4}$ alkyl groups.

2. A compound as claimed in claim 1, wherein, when A represents CH, then R$^2$ does not represent lower alkyl or H.

3. A compound as claimed in claim 1, wherein, when A represents N, R$^1$ represents lower alkyl and R$^2$ represents lower alkyl, Het, alkylHet, aryl or alkylaryl.

4. A compound as claimed in claim 1, wherein R$^1$ represents linear, branched, cyclic, or acyclic, lower alkyl, Het or alkylHet.

5. A compound as claimed in claim 1, wherein R$^2$ represents linear or branched, cyclic, acyclic, or part-cyclic, lower alkyl (which alkyl group is optionally terminated by OH), alkylHet or alkylaryl (the alkyl group of both of which is optionally interrupted by an O atom), aryl or Het.

6. A compound as claimed in claim 1, wherein R$^3$ represents linear or branched lower alkyl, optionally terminated by OR$^5$, where R$^5$ represents H or methyl.

7. A compound as claimed in claim 1, wherein R$^{12}$ and R$^{13}$ together with the nitrogen atom to which they are attached, represent 4-R¹⁴-piperazinyl, in which R¹⁴ represents H or lower alkyl, which alkyl group is optionally substituted or terminated by one or more substituents selected from aryl, Het, halo, cyano, nitro, $OR^5$, $C(O)R^6$, $C(O)OR^7$, $C(O)NR^8R^9$, $NR^{10a}R^{10b}$, $SO_2NR^{11a}R^{11b}$ and $N(H)SO_2R^{11a}$.

8. A formulation comprising a therapeutically effective amount of a compound as defined in claim 1 in admixture with a pharmaceutically or veterinarily acceptable adjuvant, diluent or carrier.

9. A formulation as claimed in claim 8, which is a pharmaceutical formulation.

10. A formulation as claimed in claim 8, which is a veterinary formulation.

11. A method of treating a medical condition for which inhibition of cGMP PDE5 is desired, which comprises administering a therapeutically effective amount of a compound as claimed in claims 1 to a patient in need of such treatment.

12. A method as claimed in claim 11, wherein the condition is male erectile dysfunction, female sexual dysfunction, benign prostatic hyperplasia (BPH), bladder cutlet obstruction, incontinence, stable or unstable variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma, a disease characterised by disorders of gut motility, pre-eclampsia, Kawasaki's syndrome, nitrate tolerance, multiple sclerosis, peripheral diabetic neuropathy, stroke, Alzheimer's disease, or acute respiratory failure.

13. A process for the preparation of a compound of formula IA, or of formula IB, as defined in claim 1, which comprises:

(a) cyclisation of a corresponding compound of formula IIA, or of formula IIB, respectively:

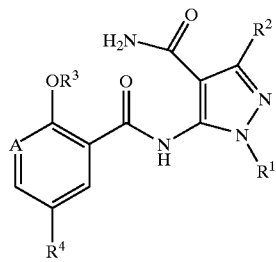

IIA

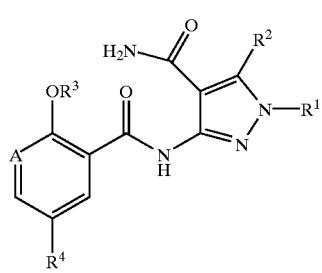

IIB wherein $R^1$, $R^2$, $R^3$, $R^4$ and A are as defined in claim 1, provided that $R^2$ is not $CH_2C(O)OR^7$ or $CH_2C(O)NR^7R^8$;

(b) cyclisation of a corresponding compound of formula VA, or of formula VB, respectively:

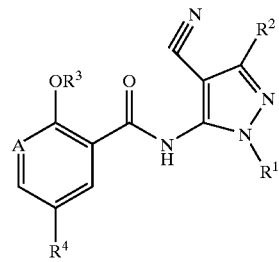

VA

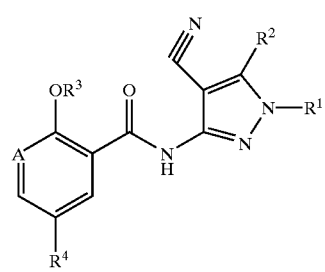

VB wherein $R^1$, $R^2$, $R^3$, $R^4$ and A are as defined in claim 1;

(c) reaction of a corresponding compound of formula VIIA, or of formula VIIB, respectively:

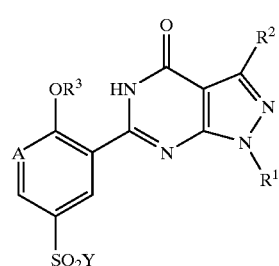

VIIA

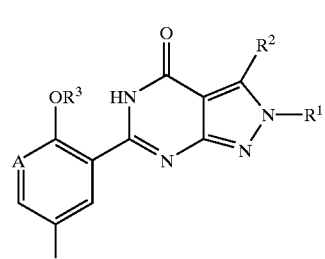

VIIB wherein Y is halo and $R^1$, $R^2$, $R^3$ and A are as defined in claim 1 with a compound of formula VIII:

$R^{12}R^{13}NH$   VIII wherein $R^{12}$ and $R^{13}$ are as defined in claim 1;

(d) for compounds of formulae IA and IB, in which $R^2$ represents lower alkyl, alkylHet or alkylaryl, reaction of a corresponding compound of formula XVIA, or of formula XVIB, respectively:

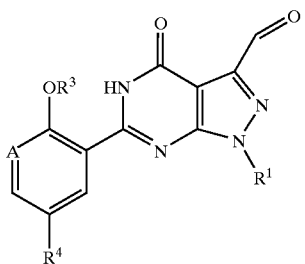

XVIA

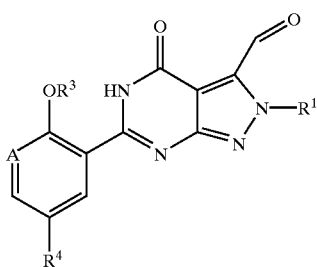

XVIB wherein $R^1$, $R^3$, $R^4$ and A are as defined in claim 1, with either an organometallic compound of formula $R^2M$, in which M represents Li or MgHal, Hal represents halo and $R^{2a}$ represents a group which provides the relevant group $R^2$ upon reaction with the —C=O group which is attached to the pyrazole ring, followed by deoxygenation of the resultant secondary alcohol, or by reductive amination using a basic compound which provides an $R^2$ group upon reaction with the —C=O group which is attached to the pyrazole ring;

(e) for compounds of formulae IA and IB in which $R^2$ represents $CH_2OH$, deprotection of a corresponding compound of formula XVIIA, or of formula XVIIB, respectively:

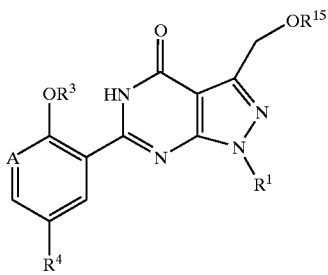

XVIIA

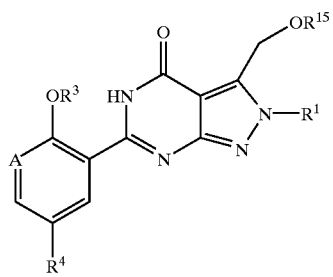

XVIIB wherein $R^1$, $R^3$, $R^4$ and A are as defined in claim 1 and $R^{15}$ represents an alcohol protecting group;

(f) for compounds of formula IA or IB in which $R^1$ represents lower alkyl, alkylHet or alkylaryl, alkylation of a corresponding compound of formula IA, or of formula IB, respectively, in which $R^1$ represents H;

(g) conversion, removal or introduction of a substituent on an aryl, or a Het, group in, or on the phenyl/pyridinyl, or pyrazolo, unit of, a compound of formula IA or IB;

(h) conversion of one $R^3$ group to another by alkoxide exchange;

(i) for compounds of formula IA or IB in which $R^{12}$ and $R^{13}$, together with the nitrogen to which they are attached, form a 4-$R^{14}$-piperazinyl group in which $R^{14}$ represents alkyl, alkylation of a corresponding compound of formula IA or IB in which $R^{14}$ represents hydrogen; or (j) deprotection of a protected derivative of a compound of formula IA or of formula IB.

14. A compound of formula IIA, or of formula IIB, as defined in claim 13.

15. A compound of formula VA, or of formula VB, as defined in claim 13.

16. A compound of formula VIIA, or of formula VIIB, as defined in claim 13 provided that said compound is not a compound of formula VIIA in which $R^1$ represents $C_{1-6}$ alkyl, $R^2$ represents H, methyl or ethyl, and $R^3$ represents $C_{2-4}$ alkyl when A represents CH.

17. A compound of formula XVIA, or of formula XVIB, as defined in claim 13.

* * * * *